(12) United States Patent
Weis et al.

(10) Patent No.: US 8,541,190 B2
(45) Date of Patent: Sep. 24, 2013

(54) METHODS AND MATERIALS FOR IN VITRO ANALYSIS AND/OR USE OF MEMBRANE-ASSOCIATED PROTEINS, PORTIONS THEREOF OR VARIANTS THEREOF

(76) Inventors: Robert M. Weis, Amherst, MA (US); Anthony L. Shrout, Easthampton, MA (US); Edward A. Esposito, Greenfield, MA (US)

( * ) Notice: Subject to any disclaimer, the term of this patent is extended or adjusted under 35 U.S.C. 154(b) by 0 days.

(21) Appl. No.: 11/823,728

(22) Filed: Jun. 28, 2007

(65) Prior Publication Data

US 2008/0003631 A1 Jan. 3, 2008

Related U.S. Application Data

(60) Provisional application No. 60/816,944, filed on Jun. 28, 2006.

(51) Int. Cl.
*C12Q 1/50* (2006.01)
(52) U.S. Cl.
USPC .............................................. 435/17; 435/7.8
(58) Field of Classification Search
USPC .................................................... 435/17, 7.8
See application file for complete search history.

(56) References Cited

U.S. PATENT DOCUMENTS

| | | | |
|---|---|---|---|
| 4,078,052 A | 3/1978 | Papahadjopoulos | |
| 4,235,871 A | 11/1980 | Papahadjopoulos et al. | |
| 4,394,149 A | 7/1983 | Szoka, Jr. et al. | |
| 4,394,448 A | 7/1983 | Szoka, Jr. et al. | |
| 4,429,008 A | 1/1984 | Martin et al. | |
| 4,565,696 A | 1/1986 | Heath et al. | |
| 4,598,051 A | 7/1986 | Papahadjopoulos et al. | |
| 4,755,388 A | 7/1988 | Heath et al. | |
| 5,047,513 A | 9/1991 | Dobeli et al. | |
| 5,962,641 A | 10/1999 | Nelson et al. | |
| 6,071,533 A | 6/2000 | Papahadjopoulos et al. | |
| 6,210,707 B1 | 4/2001 | Papahadjopoulos et al. | |
| 6,214,388 B1 | 4/2001 | Benz et al. | |
| 6,426,086 B1 | 7/2002 | Papahadjopoulos et al. | |
| 7,678,539 B2 * | 3/2010 | Fang et al. | 435/4 |
| 2005/0148038 A1 | 7/2005 | Weis et al. | |
| 2005/0170509 A1 | 8/2005 | Papahadjopoulos et al. | |

FOREIGN PATENT DOCUMENTS

| | | | |
|---|---|---|---|
| JP | WO2005007679 A1 * | 1/2005 | |
| WO | 2005037858 | 4/2005 | |

OTHER PUBLICATIONS

Alarcon, B. Gil, D., Delgado, P., Schamel. W. W. A. Initiation of TCR Signaling: Regulation Within CD3 Dimers. Immunological Reviews 2003, vol. 191, pp. 38-46.
Basu, J. Protein Palmitoylation and Dynamic Modulation of Protein Function. Current Science, vol. 87, No. 2, Jul. 25, 2004.
Bazan-Socha, S., Bukiej, A., Marcinkiewicz, C., Musial J. Integrins in Pulmonary Inflammatory Diseases. Current Pharmaceutical Design, 2005, 11, 893-901.
Ben-Shlomo, I., Hsu, S.Y., Rauch, R., Kowalski, H.W., Hsueh A.J. Signaling Receptome: A Genomic and Evolutionary Perspective of Plasma Membrane Receptors Involved in Signal Transduction. Sci STKE, Jun. 17, 2003, 187/re9.
Brandts, J.F., Jacobson, B.S. A General Mechanism for Transmembrane Signaling Based on Clustering of Receptors. Survey and Synthesis of Pathology Research 2:107-114 (1983).
Dietrich, L.E.P., Ungermann, C. On the Mechanism of Protein Palmitoylation. European Molecular Biology Organization, vol. 5, No. 11, 2004, pp. 1053-1057.
Duzgunes, N. Preparation and Quantitation of Small Unilamellar Liposomes and Large Unilamellar Reverse-Phase Evaporation Liposomes. Duzgunes, N., ed. Part A, Methods in Enzymology, vol. 367, 2003, pp. 23-27, Amsterdam: Elsevier/Academic Press.
Duzgunes, N. Fluorescence Assays for Liposome Fusion. Duzgunes, N., ed. Part D, Methods in Enzymology, vol. 372, 2003, pp. 260-274, Amsterdam: Elsevier/Academic Press.
Discher, D.E., Eisenberg, A. Polymer Vesicles. Science, vol. 297, Aug. 9, 2002, 967-973.
Boulanger, M.J., Garcia, K. C. Shared Cytokine Signaling Receptors: Structural Insights from the GP130 System. Garcia, K, ed. Cell Surface Receptors. Advances in Protein Chemistry, vol. 68, 2004, pp. 107-146. Richards, F.M., Eisenberg, D.S., and Kuriyan J., Series Eds. Amsterdam: Elsevier/Academic Press.
Godl, K., Wissing, J., Kurtenbach, A., Habenberger, P., Blencke, S., Gutbrod, H., Salassidis, K., Stein-Gerlach, M., Missio, A., Cotten, M., Daub, H. An Efficient Proteomics Method to Identify the Cellular Targets of Protein Kinase Inhibitors. PNAS, Dec. 23, 2003, vol. 100, No. 26, 15434-39.
Heldin, C-H. Dimerization of Cell Surface Receptors in Signal Transduction. Cell, vol. 80, Jan. 27, 1995, 213-223.
Mann, M., Jensen O.N. Proteomic Analysis of Post-translational Modifications. Nature Biotechnology, vol. 21, Mar. 2003, 255-261.
Martin M.U., Wesche H. Summary and Comparison of the Signaling Mechanisms of the Toll/Interleukin-1 Receptor Family. Biochimica et Biophysica Acta 1592, 2002, 265-280.
Mui, B., Chow, L., Hope M.J. Extrusion Technique to Generate Liposomes of Defined Size. Part A, Methods in Enzymology, vol. 367, 2003, pp. 3-14, Duzgunes, N., ed. Amsterdam: Elsevier/Academic Press.
Niu, X-L., Peters, K.G., Kontos, C.D. Deletion of the Carboxyl Terminus of Tie2 Enhances Kinase Activity, Signaling and Function. Journal of Biological Chemistry. vol. 277, No. 35, Issue of Aug. 30, 2002, 31768-773.

(Continued)

*Primary Examiner* — Bin Shen
(74) *Attorney, Agent, or Firm* — Krieg DeVault LLP

(57) ABSTRACT

Methods and materials use template-directed assembly of polypeptides and optionally additional reagents to analyze the functionality of membrane-associated proteins, such as, for example, portions of transmembrane proteins, membrane-associated proteins, and others proteins that bind to transmembrane proteins and membrane-associated proteins, and to analyze the effect of test compounds or mutations on the functionality of same. The methods and materials of the present application provide a more native-like environment for analyzing the functionality of membrane-associated proteins, and thus provide effective tools for studies involving the detection of the level of enzyme activity of such proteins in an environment that closely resembles the native environment in the cell, and for novel manufacturing processes.

20 Claims, 4 Drawing Sheets

(56) References Cited

OTHER PUBLICATIONS

Pawson T., Nash, P. Assembly of Cell Regulatory Systems Through Protein Interaction Domains. Science, vol. 300, Apr. 18, 2003, 445-452.

Penuel, E., Schaefer, G., Akita, R.W., Sliwkowski, M.X. Structural Requirements for ErbB2 Transactivation. Seminars in Oncology vol. 28, No. 6, Dec. 18, 2001, pp. 36-42.

Robertson, S.C., Tynan, J.A., and Donoghue, D.J. RTK Mutations and Human Syndromes—When Good Receptors Turn Bad. Trends in Genetics, Jun. 2000, vol. 16, No. 6, pp. 265-271.

Singer, S.J., Nicolson, G.L. The Fluid Mosaic Model of the Structure of Cell Membranes. Science, vol. 175, Feb. 18, 1972, 720-731.

Shrout, A.L., Montefusco, D.J., Weis, R.M. Template-directed Assembly of Receptor Signaling Complexes. Biochemistry 2003, 42, 13379-13385.

Stroud, R.M., Wells, J.A. Mechanistic Diversity of Cytokine Receptor Signaling Across Cell Membranes. Sciences STKE 2004/231, re7.

Tuthill, T.J., Bubeck. D., Rowlands, D.J., Hogle, J.M. Characterization of Early Steps in the Poliovirus Infection Process: Receptor-Decorated Liposomes Induce Conversion of the Virus to Membrane-Anchored Entry-Intermediate Particles. Journal of Virology, Jan. 2006, p. 172-180.

Zhang, X., Gureasko, J., Shen, K., Cole, P.A., Kuriyan, J. An Allosteric Mechanism for Activation of the Kinase Domain of Epidermal Growth Factor Receptor. Cell 125, Jun. 16, 2006, p. 1137-1149.

Tuthill, Tobias J. et al: "Characterization of Early Steps in the Poliovirus Infection Process: Receptor-Decorated Liposomes Induce Conversion of the Virus to Membrane-Anchored Entry-Intermediate Particles." J. of Virology, vol. 80, No. 1, Jan. 2006, pp. 172-180.

Zhang, Xuewu et al: "An Allosteric Mechanism for Activation of the Kinase Domain of Epidermal Growth Factor Receptor." Cell, vol. 125, No. 6, Jun. 16, 2006, pp. 1137-1149.

Waters, E.K. et al: "Restoring Full Biological Activity to the Isolated Ectodomain of an Integral Membrane Protein." Biochemistry, Am. Chemical Society, Easton, PA.; US, vol. 45, No. 11, Feb. 25, 2006, pp. 3769-3774.

Bubeck, D., Filman, DJ., Hogle, JM. Cyro-electron microscopy reconstruction of a poliovirus-receptor-membrane complex. Nature Structural and Molecular Biology, 2005, vol. 12, pp. 615-618.

Changeux, JP., Thiery, J., Tung, Y., Kittel, C. On the cooperativity of Biological Membranes. Proc. Natl. Acad. Sci. USA, vol. 57, 1967, pp. 335-341.

Changeux, JP., Edelstein, SJ. Allosteric Mechanisms of Signal Transduction. Science, vol. 308, 2005, pp. 1424-1428.

Grasberger, B., Minton, AP., Delisi, C., Metzger.H. Interaction of between proteins localized in membranes. Proc. Natl. Acad. Sci. USA, vol. 83, 1986, pp. 6258-6262.

Kornberg, RD., McConnell, HM. Lateral diffusion of phospholipids in a vesicle membrane. Proc. Natl. Acad. Sci, USA, vol. 68, 1971, pp. 2564-2568.

Koshland, DE, Jr., Nemethy, G., Filmer, D. Comparison of experimental binding data and theoretical models in proteins containing subunits. Biochemistry, vol. 5, 1966, pp. 365-385.

Lim WA. The modular logic of signaling proteins: building allosteric switches from simple binding domains. Cur. Opin. Struct. Biol., vol. 12, 2002, pp. 61-68.

Monod, J., Wyman, J., Changeux, JP. On the nature of allosteric transitions: a plausible model. Journal of Molecular Biology, vol. 12, 1965, pp. 88-118.

Uzgiris, EE., Kornberg, RD. Two-dimensional crystallization technique for imaging macromolecules, with application to antigen-antibody-complement complexes. Nature, vol. 301, Jan. 13, 1983, pp. 125-129.

Thess, A., Hutschenreiter, S., Hofmann, M., Tampe, R., Baumeister, W., Guckenberger, R. Specific orientation and two-dimensional crystallization of the proteasome at metal-chelating lipid interfaces. The Journal of Biological Chemistry, vol. 277, No. 39, Sep. 27, 2002, pp. 36321-36328.

Smith, LM., Parce, JW., Smith, BA., McConnell, HM. Antibodies bound to lipid haptens in model membranes diffuse as rapidly as the lipids themselves. Proc. Natl. Acad. Sci. USA, vol. 76, No. 9, Sep. 1979, pp. 4177-4179.

Shimizu, TS., Le Novere, N., Levin, ME., Beavil, AJ., Sutton, BJ., Bray, D. Molecular model of a lattice of signalling proteins involved in bacterial chemotaxis. Nature Cell Biology, vol. 2, Nov. 2000, pp. 792-796.

Frey, W., Schief, WR., Pack, DW., Chen, C-T., Chilkoti, A., Stayton, P., Vogel, V., Arnold, FH. Two-dimensional protein crystallization via metal-ion coordination by naturally occurring surface histadines. Proc. Natl. Acad. Sci. USA, vol. 93, May 1996, pp. 4937-4941.

Celia, H., Wilson-Kubalek, E., Milligan, RA., Teyton, L. Structure and function of a membrane-bound murine MHC class 1 molecule. Proc. Natl. Acad. Sci. USA, vol. 96, May 1999, pp. 5634-5639.

Changeux, J-P., Edelstein, SJ. Allosteric mechanisms in normal and pathological nicotinic acetylcholine receptors. Current Opinion in Neurobiology, vol. 11, 2001, pp. 369-377.

Changeux, J-P., Edelstein, SJ. Allosteric receptors after 30 years. Neuron, vol. 21, Nov. 1998, pp. 959-980.

Farrens, DL., Altenbach, D., Yang, K., Hubbell, WL., Khorana, HG. Requirement of rigid-body motion of transmembrane helices for light activation of Rhodopsin. Science, vol. 274, 1996, pp. 768-770.

Francis, NR., Levit, MN., Shaikh, TR., Melanson, LA., Stock, JB., Derosier, DJ. Subunit organization in a soluble complex of tar, CheW, and CheA by Electron Microscopy. The Journal of Biological Chemistry, vol. 277, No. 39, Sep. 27, 2002, pp. 36755-36759.

Liu, Y., Levit, M., Lurz, R., Surette, MG., Stock, JB. Receptor-mediated protein kinase activation and the mechanism of transmembrane signaling in bacterial chemotaxis. EMBO Journal, vol. 16, No. 24, 1997, pp. 7231-7240.

Levit, M. Liu, Y. Stock, JB. Mechanism of CheA protein kinase activation in receptor signaling complexes. Biochemistry, vol. 38, 1999, pp. 6651-6658.

Li, G., Weis, RM. Covalent modification regulates ligand binding to receptor complexes in the chemosensory system of Escherichia coli. Cell, vol. 100, Feb. 4, 2000, pp. 357-365.

Dietrich, C., Boscheinen, O., Scharf, KD., Schmitt, L., Tampe, R. Functional immobilization of a DNA-binding protein at a membrane interface via histidine tag and synthetic chelator lipids. Biochemistry, vol. 35, No. 4, 1996, pp. 1100-1105.

Farsad, K., Ringstad, N., Takei, K., Floyd, Sr., Rose, K., De Camilli, P. Generation of high curvature membranes mediated by direct endophilin bilayer interactions. The Journal of Cell Biology, vol. 155, No. 2, Oct. 15, 2001, pp. 193-200.

Yamamoto, S., Kubotsu, K., Kida, M., Kondo, K., Matsuura, S., Uchiyama, S., Yonekawa, O., Kanno, T. Automatred homogeneous liposome-based assay system for total complement activity. Clinical Chemistry, vol. 41, No. 4, 1995, pp. 586-590.

Wu, J., Li, J., Li, G., Long, DG., Weiss, RM. The receptor binding site for the methyltransferase of bacteria chemotaxis is distinct from the sites of methylation. Biochemistry, vol. 35, No. 15, 1996, pp. 4984-4993.I.

Schmitt, L., Dietrich, C., Tampe, R. Synthesis and characterization of chelator-lipids for reversible immobilization to engineering proteins at self-assembled lipid interfaces. J. Am. Chem. Soc., vol. 116, No. 19, 1994, pp. 8485-8491.

Dietrich, C., Schmitt, L., Tampe, R. Molecular organization of histidine-tagges biomolecules at self-assembled lipid interfaces using a novel class of chelator lipids. Proc. Natl. Acad. Sci. USA, vol. 92, Sep. 1995, pp. 9014-9018.

Kubalek, E.W., Le Grice, S.F.J., Brown, P.O. Two-dimensional crystallization of histidine-tagged, HIV-1 reverse transcriptase promoted by a novel nickel-chelating lipid. Journal of Structural Biology, vol. 113, 1994, pp. 117-123.

\* cited by examiner

METHODS AND MATERIALS FOR IN VITRO ANALYSIS AND/OR USE OF MEMBRANE-ASSOCIATED PROTEINS, PORTIONS THEREOF OR VARIANTS THEREOF

CROSS-REFERENCE TO RELATED APPLICATIONS

The present application claims the benefit of U.S. Provisional Patent Application No. 60/816,944 filed 28 Jun. 2006, which is hereby incorporated by reference in its entirety.

BACKGROUND

The present application relates to the field of biotechnology, and in particular, to fields involving the study and use of membrane-associated proteins.

All living organisms are composed of cells, from single celled organisms such as bacteria, to the complex cellular architecture of humans. The cells include multifaceted, chemically driven systems, such as, for example, communication networks that control a cell's response to external stimulus. Signal transduction pathways involve protein 'teams' that work in concert to execute desired pathway instructions, such as, for example, gene regulation, cell growth, movement, and hormone release.

Cell membranes are bilayers of lipid molecules that define the boundary between, and serve as selective barriers between, the inside and outside of all cells and between the inside and outside of cellular compartments (organelles). Similar membranes also define the boundary between the inside and outside of some viruses. A wide variety of proteins are embedded in or on, or associated with, the cell membrane, thereby creating a highly specialized environment. It is widely accepted that the membrane environment, including the proteins and assemblies of proteins that naturally occur in and on the membrane, is essential for normal biological function. For example, a significant portion of these membrane proteins are responsible for the process of transmembrane signaling, which conveys information across the membrane, frequently, although not exclusively, from the outside of the cell to the inside. The membrane can be likened to a two-dimensional fluid sheet, which serves as the natural template for the assembly of signal transduction elements. The association of these proteins with the membrane in essence restricts their motion to two dimensions rather than three, which promotes interactions between proteins that are necessary for proper assembly and function.

Typically, transmembrane signaling proteins are the transducers of the initial stimuli that set cellular pathways in motion. The signal transduction pathways in which the transmembrane signaling events are a part, are critical for generating responses to broad range of external stimuli that are generally recognized to be generated either by the organism itself (hormones, growth factors, other cells) or from foreign entities (foreign cells or cells recognized as foreign, viruses, bacteria, other pathogens and pathogenic materials, and allergens). Transmembrane signaling and signal transduction pathways are also indispensable for communication among cells in multicellular organisms. Consequently, almost all processes critical to the growth and function of multicellular organisms depend on transmembrane signaling. When these communication networks fail to execute an instruction, or when signaling becomes deregulated, diseases result, such as, for example, cancer, diabetes, and obesity. To illustrate the crucial role of cell signaling in disease, it has been reported that greater than 60% of all drugs, including drugs available in the marketplace and drugs that have been selected for market, target proteins involved in signal transduction pathways. With an estimated annual spending on early stage drug screening in excess of one billion dollars, there is a great need for innovations that improve the efficiency and accuracy of such screening assays.

"Transmembrane receptors" are key protein elements in the process of signal transduction. The receptors often span the membrane bilayer one or more times in order to convey information across it during the process of transmembrane signaling. It is widely known that membrane receptors interact with one another by clustering together in the membrane to form dimers, trimers, or more generally oligomers, and that the process of clustering and/or the formation of multimers is an integral part of the transmembrane signaling process. Dimers, are often generated through the association of two identical protein molecules to form homodimers, but heterodimers can form in other instances, through the specific association of two different receptors (See, e.g., Martin and Wesche, 2002; Bazan-Socha et al. 2005; Penuel et al., 2001). More generally hetero-oligomeric complexes form to orchestrate the transmembrane signaling. (See, e.g., Alarcon et al., 2003). Also, additional proteins involved with the process of transmembrane signaling have been reported to associate with the inner leaflet of the membrane through specific interactions with the receptor and/or the membrane itself. (See, e.g., Pawson and Nash, 2003). These too are part of the process of signal transduction.

Genome sequencing projects have produced a wealth of information that have brought about significant advances in descriptive cellular and molecular biology, including the establishment of familial and evolutionary classifications of a multitude of transmembrane receptors. (See, e.g., Ben-Shlomo et al., 2003). These works, along with the continuing efforts to determine the structures and functions of transmembrane receptors, have, altogether, led to the identification of unifying principles in the processes of transmembrane signaling, principles that are inextricably associated the special properties of the cell membrane.

Significant resources and attention have been devoted to the study of membrane-associated proteins; however, membrane samples of the proteins that are used in such biochemical experiments are frequently isolated from cells expressing the receptor at elevated levels, which can result in complex and heterogeneous samples. Also, receptor reconstitution is labor-intensive, and the conditions that maintain a high level of activity while also preserving the vectoral and lateral organization required for function can be difficult to find. Notably, it is the very association of receptors with membranes that invariably requires the use of detergent for the purification of receptors, which leads to well-known difficulties, including low yield and the disruption of critical protein-protein interactions. Low yields are typical and represent a major impediment to widespread use of such receptors in cell-free assay systems. Also, the solubilizing activity of detergents, which is the basis of their usefulness in other applications, such as membrane protein purification, represents a significant disadvantage in functional assays where protein-protein interactions are necessary. In this setting, detergents disrupt necessary interactions between the receptors in the membrane, as well as the interactions between receptors and receptor-associated proteins, and protein-protein interactions in general. While formulations of detergent compatible with functional activity can sometimes be achieved, these are identified only by time-consuming and case-specific methods, and the level of activity usually achieved often remains less than satisfactory.

To overcome these difficulties, researchers have attempted to identify key regions of the membrane-associated proteins that can be cloned out for study in vitro. Some of these receptor fragments support activity and have been commercialized for the study of pair-wise interactions, such as, for example, interactions between a protein domain that possesses enzymatic activity and a substrate. Much information has been lost in these situations, however, as signaling proteins are studied in environments that differ significantly from their natural, cellular environments.

It is apparent from the above that there is a continuing need for advancements in the relevant field, including new methods and materials for restoring function to membrane-associated proteins outside their natural, cellular environment. The present application addresses this need.

SUMMARY

Using template-directed assembly of proteins, protein fragments and/or variants thereof, the present application provides methods and materials useful to analyze the functionality of membrane-associated polypeptides, such as, for example, portions of transmembrane proteins, membrane-associated proteins, and other proteins that bind to transmembrane proteins and membrane-associated proteins, and to analyze the effect of spatial organization on the functionality of the polypeptides. The methods and materials described herein provide a more native-like environment for analyzing the functionality of membrane-associated proteins, and thus provide effective tools for studies involving the detection of the level of enzyme activity of such proteins in an environment that closely resembles the native environment in the cell. This in turn provides a wide variety of useful applications, such as, for example, efficient processes for analyzing how drugs, drug candidates or other active agents affect the functionality of a membrane-associated protein, fragment, or pathway.

In one aspect, the application provides a means to assemble membrane-associated polypeptides through the use of a templating material for the purpose of generating associations among polypeptides, and providing a template/polypeptide complex that has a functionality correlating to the functionality of membrane-associated polypeptides present in the native environment. The present application, in its various embodiments, can be used with components derived from a wide variety of membrane-associated protein systems, such as, for example, signaling systems that require interactions among one or more like or unlike entities at the membrane surface to activate or enhance the biological function of the components. Reported herein are multiple examples corresponding to a large variety of human membrane-associated protein systems, showing how the assembly of selected fragments thereof (polypeptides) on a two-dimensional fluid membrane-like template restores functionality to a level much closer to native levels and manners of functionality, compared to that which can be achieved in solution or dispersion. While it is not intended that the subject matter of this application be limited to any theory, it is believed that functionality in various different systems can result from (1) an orienting effect produced by assembling proteins with a template, (2) the interactions that develop through the assistance of the template to facilitate clustering of the receptor proteins or other polypeptides to form dimers, trimers and more generally oligomers, and/or (3) the recruitment of associated signaling proteins or other reagents, which are altogether referred hereto as "signaling teams." The broad utility of the methods and materials described herein is shown by the successful assembly of several human membrane-associated protein systems onto templates as described herein. The recombinant protein reagents used in experimental work reported herein are cytoplasmic domains derived from receptor-tyrosine kinases (RTKs). RTKs are a large class of transmembrane receptor proteins, which are widespread in species belonging to the eukaryotic kingdom, including humans. Representative members of the RTK class have been investigated. RTKs function in pathways linked to numerous diseases including obesity, cancer, diabetes and developmental defects. The success of these systems in providing a high level of functionality establishes that template-directed assembly of functional protein fragments and/or signaling molecules can be reliably and predictably reproduced for a wide variety of membrane-associated protein systems, even complex human systems and protein systems characteristic of other higher organisms, such as, for example, mammalian systems, on the basis of known similarities in the organization and mode of action of protein fragments derived therefrom. The high level of biological activity of the protein reagents achieved in accordance with the application is representative of a wide variety of membrane-associated protein systems of medical relevance. The present application therefore describes a significant advancement in biomedical research, and provides methods and materials that are useful in a wide variety of protocols including, for example, protocols used to screen for drugs and candidate drugs that have an effect on a selected protein or protein system.

In one aspect of the application, there is provided a method for analyzing in vitro the effect of a molecule upon an enzyme-catalyzed reaction or cascade. The method comprises: (1) providing an aqueous fluid including one or more reagent; and a biologically active complex including a template and at least one polypeptide attached to the template, wherein the complex is functional under a given set of conditions to produce a measurable modification in the content of said one or more reagent or in said polypeptide; (2) introducing a test molecule, such as, for example, a drug, drug candidate, agonist or antagonist, into the fluid; and (3) measuring the modification to determine the effect of the test molecule on the reaction or cascade. The measurable modification can result from a wide variety of processes, such as, for example, the following: (1) a chemical modification to the polypeptide, or equivalently a protein or protein domain, resulting from intrinsic enzymatic activity of said polypeptide, protein or protein domain as it interacts with the template, (2) chemical modification of a soluble substrate reagent present in the fluid that is catalyzed by the polypeptide as it interacts with the template, (3) chemical modification of a soluble substrate reagent that is catalyzed by enzymatic activity of a signaling enzyme present in the fluid and recruited to the complex, (4) chemical modification to the polypeptide in a process catalyzed by a signaling protein that is recruited to the complex, and (5) chemical modification of a soluble substrate reagent present in the fluid that results from a reaction cascade initiated by the polypeptide as it interacts with the template or a signaling enzyme that is recruited to the complex. The measurable modification of a polypeptide can be, for example, phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, activation of a fluorescent signal, release of a reaction product or utilization of a reagent initially present in the fluid. In one exemplary embodiment, the polypeptide comprises a receptor tyrosine kinase domain, and the process comprises autophosphorylation of the receptor tyrosine kinase domain.

In one embodiment, the template is a phospholipid vesicle. In other embodiments the template is a polymer vesicle, a polymer micelle, a polymer molecule, or a polymer bead. In yet other embodiments, the template is coated onto a substrate material. Substrates can be, for example, glass slides, glass beads, silicon wafers, silicon chips, planar noble metals, colloidal noble metal, metal oxide layers, nanoparticulate materials, or polymer slabs, films or beads. In these examples the template can be, for example, a phospholipid bilayer, a phospholipid monolayer or a polymer film.

In one embodiment, the polypeptide has attached thereto a linker component effective to attach the polypeptide to the template. The linker component can be, for example, a component effective to covalently bond to the template, a component effective to interact with the template noncovalently by metal chelation, a component effective to interact with the template noncovalently by other complementary interactions, or an insertion domain effective to interact with the template noncovalently by insertion of at least a portion of the domain into the template. In an embodiment in which the linker component comprises a component effective to interact with the template noncovalently by metal chelation, the metal or metal ion can be associated either with the template or with the linker component prior to the interaction. In one embodiment, the linker component comprises a genetically engineered histidine tag. In an embodiment in which the linker component comprises an insertion domain, the insertion domain can be configured to interact with the template noncovalently by insertion of at least a portion of the domain into the template, wherein at least a portion of the insertion domain interacts with the template by hydrophobic interactions. In another embodiment, the linker is an insertion domain that comprises a genetically engineered peptidyl insertion domain. The insertion domain can alternatively comprise an anchoring moiety formed by the adaptation of naturally occurring mechanisms, such as, for example, palmitoylation, myristoylation, prenylation and geranylation or through a GPI linkage. In another embodiment the anchoring moiety can be comprised of a synthetic analog of these naturally occurring mechanisms of palmitoylation, myristoylation, prenylation, and geranylation or GPI linkage. In another embodiment, the linker component comprises an engineered amphipathic helix that has affinity for the surface of the template.

In another aspect of the application, there is provided a method for determining the effect of one or more mutations on the functionality of a membrane-associated protein. It is well known to those knowledgeable of biology and medicine that amino acids substitutions, deletions, or insertions in proteins, which can be caused by mutations in the DNA from which the proteins are generated, can result in dramatic differences in the functionality of said proteins, such as for example, in a signaling pathway. The method includes: (1) providing a control complex that includes a control (e.g., nonmutated) polypeptide, the control polypeptide comprising a membrane-associated protein, a fragment thereof or a variant thereof featuring substantially normal functionality, whereby the control complex is functional under a given set of conditions to produce a measurable modification in the content of one or more reagent or in said polypeptide, the control polypeptide modified to incorporate thereon a linker component that does not substantially affect the functionality of the control polypeptide, wherein the modified control polypeptide is attached to a template; (2) providing a test complex comprising a corresponding test polypeptide featuring one or more mutations; (3) contacting the test complex and the control complex in aqueous fluids to said one or more reagent under similar reaction conditions; and (4) measuring the modification for the test complex and the control complex, and comparing same to score the functionality of the test and control polypeptides.

In another aspect of the application, there is provided a complex that includes: (1) a template; and (2) a polypeptide linked to the template, the polypeptide comprising a human membrane-associated protein, or a fragment thereof, or a polypeptide having at least about 80% identity thereto, the polypeptide having attached thereto a linker component that does not substantially affect the functionality of the polypeptide and that is effective to attach the polypeptide to the template. In one embodiment, the polypeptide is derived from a transmembrane receptor protein. In another embodiment, the polypeptide is a cytoplasmic domain derived from a receptor tyrosine kinase. In alternative embodiments, the polypeptide comprises, for example, an insulin receptor protein, an ErbB4 receptor protein, an Axl receptor protein, an EphB2 receptor protein, a fragment thereof or a functional variant thereof.

In yet another aspect, the application provides a complex that includes: (1) a template; and (2) a polypeptide comprising a protein in its entirety or its fragment, that is not a transmembrane protein, but is a protein that functions via other types of interactions with a membrane. This aspect of the application contemplates a protein that is normally associated with the membrane under resting conditions, or a protein recruited to the membrane as the result of a change in conditions, that may, for example, result from a stimulatory event. In another embodiment the protein is a membrane associated non receptor tyrosine kinase or a serine-threonine kinase. In another embodiment the protein is a member of Src family of kinases, the Lyn kinase, or the Syk kinase.

In yet another aspect, the application provides a complex that includes: (1) a template; and (2) a polypeptide having an N-terminal end linked to the template and a C-terminal end linked to the template, the N-terminal end and the C-terminal end of the polypeptide both modified to incorporate thereon a linker component that does not substantially affect the functionality of the polypeptide loop and that is effective to link the respective ends of the polypeptide to the template. In one embodiment, the polypeptide comprises a fragment of a multi-pass transmembrane protein. Such doubly anchored peptide may be derived, for example, from the cytoplasmic loops of G-coupled receptors and may serve, for example, to recruit the one or more components of the heterotrimeric G-proteins.

In yet another aspect of the application, there is provided a complex that includes: (1) a template; and (2) a plurality of different polypeptides linked to the template, each of the polypeptides modified to incorporate thereon a linker component that does not substantially affect the functionality of the polypeptide and that is effective to link the polypeptides to the template. In one embodiment, the plurality of polypeptides comprises a plurality of fragments of a multi-pass transmembrane protein. The fragments can be, for example, cytoplasmic fragments or extracellular fragments.

Another aspect of the application is a method for performing a manufacturing process that requires an assembly of one or more polypeptides on a template in a 'team', or an associated complex, which in this aspect of the application catalyzes the modification of a substrate in an effective manner. Examples of substrates contemplated by this aspect of the application include, for example, a constituent member of the assembled protein team, a portion of the template, or a reagent molecule that is separately included in the fluid in which the complex is suspended. The method comprises: (1) providing an aqueous fluid including one or more reagent; and a biologically active complex including a template and at least one polypeptide attached to the template, wherein the complex is functional under a given set of conditions to generate a reaction product that results from the functionality of the complex; and (2) isolating the reaction product. The method may also include the introduction of a substrate molecule, which may be part of the assembled team, part of the template, or a molecule added into the fluid separate from the complex, such as, for example, after the active complex is generated. In one embodiment, this aspect of the application may be applied to the synthesis of a protein that is modified post-translationally under the conditions of a team-assembled reaction. In another embodiment this aspect of the application may be used to synthesize phosphorylated receptor tyrosine kinase domains.

In still another aspect, the application provides a method for determining whether an observed disease state of a patient results from sub-standard functionality of a membrane-associated protein. The method includes: (1) providing a test complex that includes a test polypeptide isolated from a patient, the test polypeptide comprising a membrane-associated protein or a fragment thereof suspected to exhibit sub-standard functionality, the test polypeptide modified to incorporate thereon a linker component that does not substantially affect the functionality of the test polypeptide, the modified test polypeptide attached to a template; (2) providing a control complex comprising a corresponding control polypeptide featuring normal function, the control complex functional under a given set of conditions to produce a measurable modification in the content of one or more reagent or in said polypeptide under suitable reaction conditions; (3) contacting the test complex and the control complex in aqueous fluids to said one or more reagent under similar conditions; and (4) measuring the modification for the test complex and the control complex and comparing same to score the functionality of the polypeptide on the reaction or cascade.

Further embodiments, forms, features and aspects of the present application shall become apparent from the detailed description and figures provided herewith.

F: A generic illustration of noncovalent interactions between the proteinaceous entity and the template by way of an 'insertion domain'. Insertion domains are part of the proteinaceous entity that can form a noncovalent association with the template, either by penetrating into the template, by associating with the template surface, or by a combination of penetration and surface association.

Figure 4:
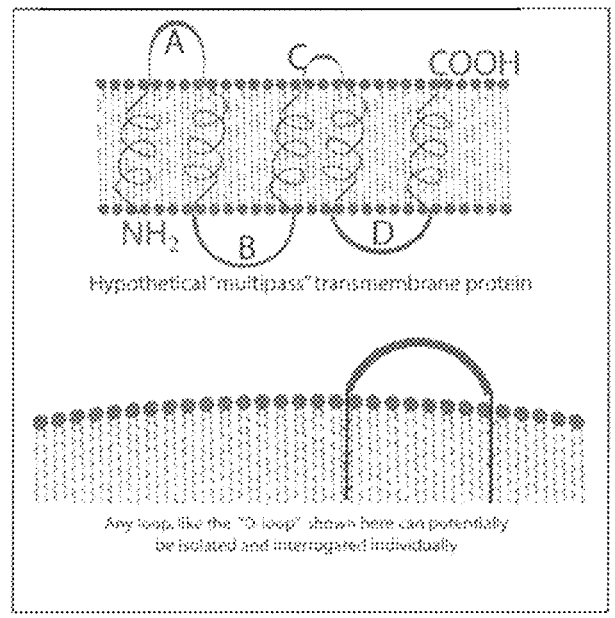

FIG. 4. Multipoint Template Attachment

A: An embodiment of the application in which the template-associable entity has more than one point of attachment to the membrane. An example of a multipass receptor protein, illustrated at the top of FIG. 4, has the extramembranous loops A, B, C and D between transmembrane segments. The lower part of FIG. 4 depicts a proteinaceous entity associated with the template at two points.

Figure 5:
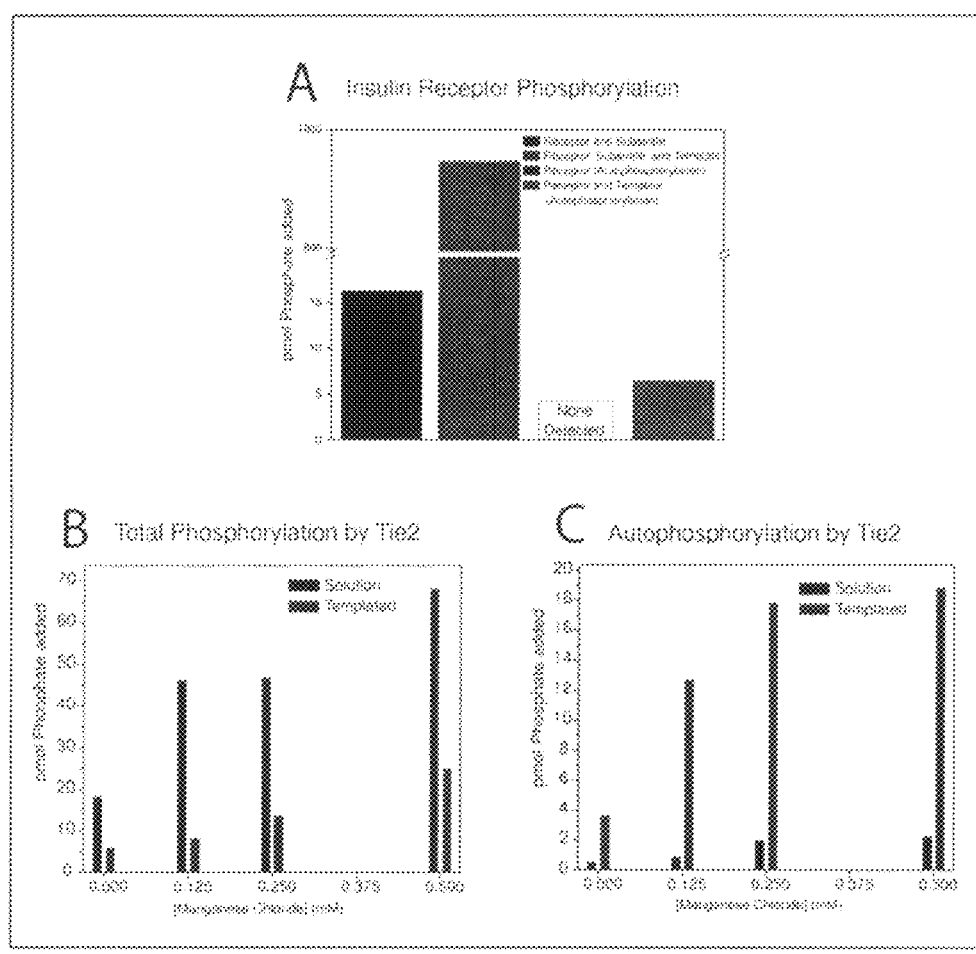

FIG. 5. Examples of Enhanced Activity with Template-Assembled Receptor Tyrosine Kinases A: Autophosphorylating and substrate-phosphorylating activities of the Insulin Receptor RTK domain. (Upstate product number 14-553). The substrate in the assay is Axltide, from Upstate (product number 12-516), which is a peptide of composition KKSRGDYMTMQIG (SEQ ID NO: 1)

Activities in solution and on templates, either with or without substrate:
1. Left-most Column: Insulin RTK domain plus exogenous substrate (Axltide) in solution (no template).
2. Second Column from Left: Insulin RTK domain plus exogenous substrate (Axltide) in the presence of template.
3. Second Column from Right: Insulin RTK domain (no exogeneous substrate) in solution.
4. Right-most Column: Insulin RTK domain (no exogeneous substrate) in the presence of template.

B: The autophosphorylating activity, measured as pmol of acid precipitatable phosphate at 10 min., of the Tie2 RTK domain plus the substrate-phosphorylating of the Tie2 RTK domain. The histogram shows the dependence of the activity on $MnCl_2$ concentration. Results of measurements at each concentration of $MnCl_2$ are provided by a pair of bars, the left bar of each pair representing the activities measured in solution and the right bar of each pair representing the activities measured in the presence of template. The Tie2 RTK domain is an Upstate (product number 14-540), and the substrate is poly([Glu]$_4$Tyr) (poly(SEQ ID NO: 2)) from Sigma-Aldrich (product number P7244).

C: The autophosphorylating activity of the Tie2 RTK domain, measured as pmol of acid precipitatable phosphate at 10 min., either in solution (left bar of each pair) or in the presence of template (right bar of each pair). The Tie2 RTK domain is an Upstate reagent, product number 14-540. The histogram shows the dependence of the activity on $MnCl_2$ concentration.

Figure 6:
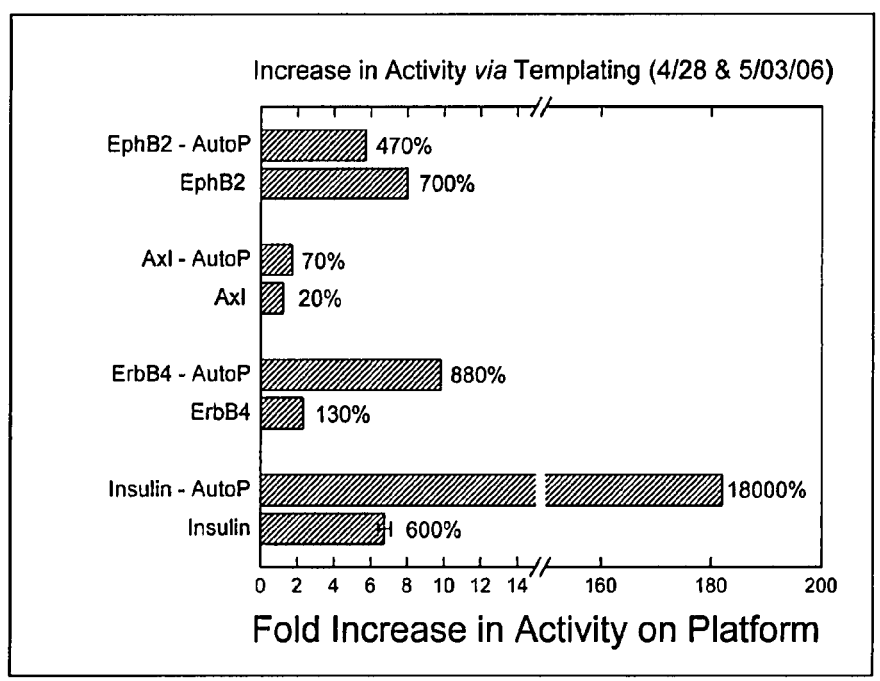

FIG. 6. Fold Increase in Phosphorylation Activity Produced by Template Directed Assembly of Selected Tyrosine Kinase Domains EphB2 RTK domain (Upstate product number 14-553), with or without poly([Glu]$_4$Tyr) (poly(SEQ ID NO: 2)) substrate (Sigma-Aldrich product number P7244); Axl RTK domain (Upstate product number 14-512), with or without Axltide substrate (Upstate product number 12-516); ErbB4 RTK domain (Upstate product number 14-569), with or without poly([Glu]$_4$Tyr) (poly(SEQ ID NO: 2))substrate (Sigma-Aldrich product number P7244); Insulin Receptor RTK domain (Upstate product number 14-553), Axltide substrate (Upstate product number 12-516).

DEFINITIONS

Axltide. Is an example of an oligopeptide that has the specific sequence KKSRGDYMTMQIG. (SEQ ID NO: 1) K is the one letter abbreviation for the amino acid lysine, S is the one letter abbreviation for the amino acid serine, R is the one letter abbreviation for the amino acid arginine, G is the one letter abbreviation for the amino acid glycine, D is the one letter abbreviation for the amino acid aspartate, Y is the one letter abbreviation for the amino acid tyrosine, M is the one letter abbreviation for the amino acid methionine, T is the one letter abbreviation for the amino acid threonine, Q is the one letter abbreviation for the amino acid glutamine, and I is the one letter abbreviation for the amino acid isoleucine. Thus, KKSRGDYMTMQIG, (SEQ ID NO: 1) represents an oligopeptide that consists of $H_2N$-lysine-lysine-serine-arginine-glycine-aspartate-tyrosine-methionine-threonine-methionine-glutamine-isoleucine-glycine-COOH, where $H_2N$ and COOH are used to denote the amino and carboxy termini of the oligopeptide, respectively. Axltide, as defined here, is a model substrate of the Axl receptor tyrosine kinase and the insulin receptor tyrosine kinase.

Poly[(glu)$_4$tyr]$_n$(Poly[SEQ ID NO: 2]$_n$). A synthetic polypeptide comprised of repeating units of "glutamate-glutamate-glutamate-glutamate-tyrosine" of the form $H_2N$ (glutamate-glutamate-glutamate-glutamate-tyrosine)$_n$-COOH, where n is meant to signify the number of the repeating units that are joined together, and typically has a value between 4 and 30.

Polypeptide. Polypeptides are polyamide polymers, which typically, but not always, consist of two or more amino acids of the L-enantiomeric form of alpha amino acids. Variations include, but are not limited to the D-enantiomeric forms of alpha amino acids and amino acids with unnatural side chains. It is the intention of this definition to include naturally occurring proteins and proteineacous entities. In addition the definition is intended include materials that are not considered to be fully functional proteins, such as for example peptides, oligopeptides and hybrid molecules of which polypeptides constitute only a part. Polypeptides can be generated by (1) chemical synthesis, (2) in vitro translation, (3) in vivo synthesis through the use of protein engineering and molecular biology, or (4) isolation from naturally occurring sources.

Protein. Typically, but not exclusively refers to a polypeptide of natural origin. A protein is typically but not exclusively of sufficient length to adopt well-defined tertiary structure. The terms protein, protein domain, and protein fragment are used interchangeably. Proteins that possess catalytic activity are enzymes.

Team. A signaling team is typically, but not limited to, proteins and protein fragments that function together in a way that the individual elements, of which the team consists, could not. In preferred embodiments the elements of the team are proteins, protein domains and polypeptides. In other embodiments of the application the elements of the team can also include lipids, carbohydrates, nucleic acids and other prosthetic groups that are either covalently or noncovalently associated with protein components of the team.

Template. A template is a molecular entity, either naturally occurring, synthetic or a hybrid of natural and synthetic parts, which facilitates functional interactions between the participating elements of a biochemical process. In one embodiment, the participating elements of a biochemical process are proteins and protein fragments that function together in cellular signal transduction pathways. In one embodiment, the template is a phospholipid membrane, arranged as a liposome, which has elements that facilitate the assembly of the participating elements.

With reference to the figures and accompanying discussion and examples, abbreviations used herein include: DOPC, 1,2-dioleoyl-sn-glycero-3-phosphocholine; DOGS-NTA, 1,2-dioleoyl-sn-glycero-3-{[N(-amino-1-carboxypentyl)-iminodiacetic acid]-succinyl}ammonium salt); DOGS-NTA-$Ni^{2+}$, DOGS-NTA Nickel Salt; SUV, small unilamellar vesicle; LUV, large unilamellar vesicle; Ni-NTA, nickel-nitrilotriacetic acid; ATP, adenosine triphosphate; ADP, adenosine diphosphate; GTP, guanosine triphosphate; GDP, guanosine diphosphate

DETAILED DESCRIPTION

For the purposes of promoting an understanding of the principles described herein, reference will now be made to the embodiments set forth herein and specific language will be used to describe the same. It will nevertheless be understood that no limitation of the scope of the present application is thereby intended. Any such alterations and further modifications in the described devices, systems, processes and methods, and such further applications of the principles described herein are contemplated as would normally occur to one skilled in the art to which this application relates.

The present application provides methods and materials involving analytical processes and manufacturing processes that require in vitro activity of membrane-associated polypeptides, such as, for example, portions of transmembrane proteins, membrane-associated proteins, variants thereof, and other proteins that bind to transmembrane proteins and membrane-associated proteins in vivo. One application of the methods and materials described herein involves the use of functional polypeptides in vitro to study the effect of one or more active agents on the functionality of the polypeptides, for example during screening protocols for assessing the efficacy of large numbers of drug candidates with respect to a given membrane-associated protein system. The application provides a native-like environment in vitro for performing the functionality analysis, and thus provides effective tools for studies involving the detection of enzyme activity levels in an environment that closely resembles the native environment of a cell. Another application of the methods and materials described herein involves the assembly of functional proteins in vitro for the manufacture of reagents that require the use of a reaction cascade involving functional membrane-associated proteins, or that can be more economically achieved using such proteins. As described herein, a homogeneous or heterogeneous template can be used to assemble polypeptides, and optionally additional reagents, to provide a functional complex exhibiting the biochemical activity of a membrane-associated protein or protein system, such as, for example, a signaling pathway. The complex can be used to analyze the effect of an active agent on the functionality of the protein or protein system, to analyze the effect of a mutation on the protein or protein system, or to produce reaction products of value in a novel manufacturing process.

The templates described herein provide a synthetic environment that mimics organization and asymmetry inherent in cell membranes, which creates an environment in which receptor proteins can exhibit their native functionality (such as, for example, effectively convey information between the inside and outside of the cell), and in which other types of proteins can more readily assemble for other types of function than could occur in solution. The reduction in the degrees of freedom experienced by transmembrane and peripheral membrane proteins provides a strong driving force for lateral organization, which can be essential for function, e.g. ligand-induced clustering.

Figure 1:
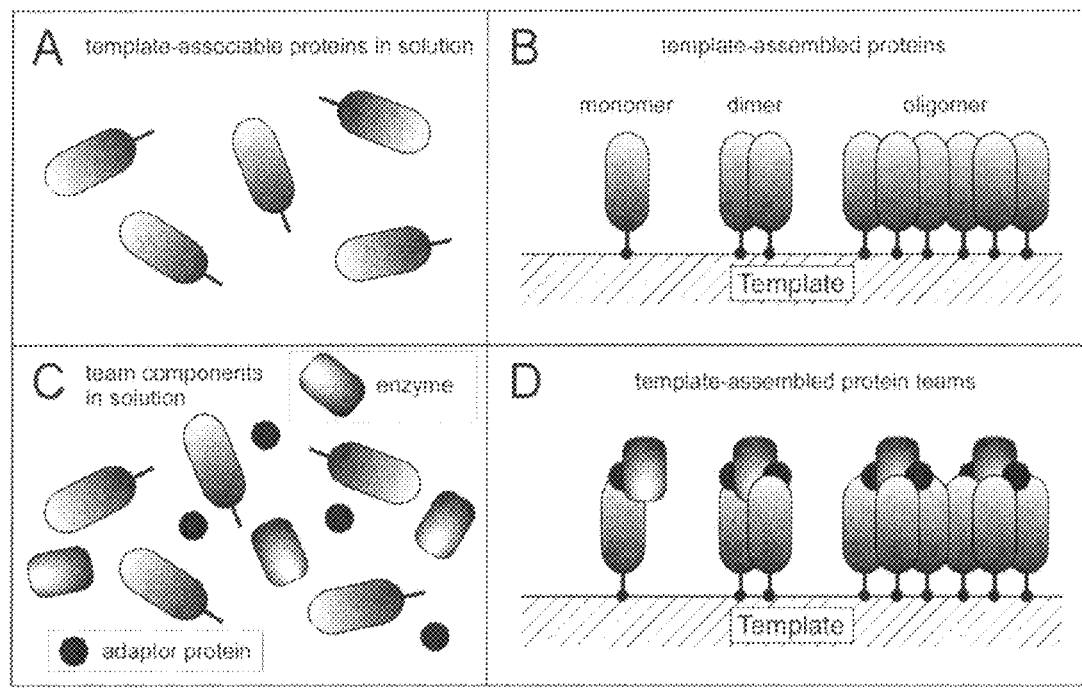
FIG. 1.
A: Proteins, protein domains or other protein fragments typically have little tendency to organize in solution.
B: The template facilitates the assembly of one or more kinds of proteinaceous entities into functional units. An interaction between the template and the proteins localize them at the surface and orients them; this promotes the formation of functional units, e.g. dimers, or more generally oligomers. Generally, but not exclusively, interactions between the template-assembled entities are essential for function.
C: Mixtures of proteins, protein domains and other protein fragments, which have functional activity in an assembled form often have little tendency to organize in solution. Without the full complement of interactions, the protein mixtures do not display the essential biological function.
D: The template facilitates the assembly of a mixture of protein domains, adaptor proteins, signaling enzymes and other proteinaceous entities into functional units. One or more proteinaceous entities in the mixture interact specifically the template (these components are 'template-associable' as in FIG. 1A), which form an assembly that recruits adaptor proteins, and other signaling proteins, to form a functioning assembly.

Membrane-associated proteins often need other 'team members' organized in the appropriate fashion to become fully functional. This activity typically arises from the assembly of a complex of proteins, which is referred to herein as 'a signaling team' that forms on or near the membrane surface. This illustrates and underscores the fundamental flaw in the prior attempts to restore functionality of membrane-associated proteins in vitro. The membranous environment provides the necessary chemical setting to assemble large teams of proteins for biologically relevant signaling. As depicted in FIG. 1 this cannot be achieved by analysis of single proteins interacting with a single partner in solution as these proteins have lost the two-dimensional information afforded by the membrane surface.

In accordance with the present application, template-directed assembly methods and materials are used to provide functional complexes in vitro of such membrane-associated protein systems in which complexes of multiple components, either transient or stable, are required for activity. The binding of a protein or suitable protein fragment to a template promotes a lateral organization among components, such as, for example, cytoplasmic fragments of transmembrane signaling proteins, that resembles the organization of cytoplasmic domains in the receptor-containing membranes of cells.

A functional protein complex in vitro provides two desired features. First, the complex exhibits activity measurably greater than would the same reagents in solution without a template (i.e., activity closer to the activity of the corresponding membrane-associated protein system in vivo). Here, greater activity may, in addition, refer to a more consistent regulation of a biological functionality similar to that which is observed in the cell, and therefore does not simply mean an increase in the magnitude of an enzyme activity. Second, the activity of the complex results in a measurable change to a test sample when the complex is placed in a solution containing the reagents necessary for the complex to function. As used herein, the phrase "measurably greater" is used to indicate that the complex has an activity at least about fifty percent greater than the activity of the same reagents in solution without a template, as measured by various methods that are known to those skilled in the art. For example, progress toward the completion of a reaction, or the rate of product formation as in the generation of post-translationally modified polypeptide, are two such examples. Here, post-translationally modified polypeptide can be taken to mean the phosphorylation of amino acid side chains, most typically on tyrosine, serine or threonine. More generally it should be evident that numerous other products of biochemical reactions can be measured, for example, but not limited to, protein phosphorylation, dephosphorylation, ATP hydrolysis, GTP hydrolysis, acylation, ubiquitination and methylation.

The diversity of signal transduction pathways gives rises to numerous embodiments that use a template to achieve functional interactions, which would not emerge with the isolated components in solution. The term "template" is used to refer to a material or an agent that facilitates the creation of relevant functional interactions. FIG. 1 is provided to illustrate the function of a template, but at the same time the illustrations of template in FIG. 1 are in no manner meant to confer a specific geometry, topology or structure to the template. FIG. 1B illustrates the generation of functional interactions by recruiting one or more proteinaceous entities from solution (FIG.

1A) through an association with the template. Interactions, for example, include homo- and hetero-dimer, trimer and oligomer formation among the template-associated species. FIG. 1D illustrates the manner in which a 'team' or 'complex' of proteins form through the assistance of a template, from a mixture of unassociated or partly associated proteins in solution (FIG. 1C), through the association of one or more kinds proteinaceous entities with the template, one more kinds of adaptor proteins and one or more membrane-associated proteins, which are recruited through an interaction with the template-associated entities. These recruited entities may or may not possess an intrinsic enzymatic activity.

Figure 2:
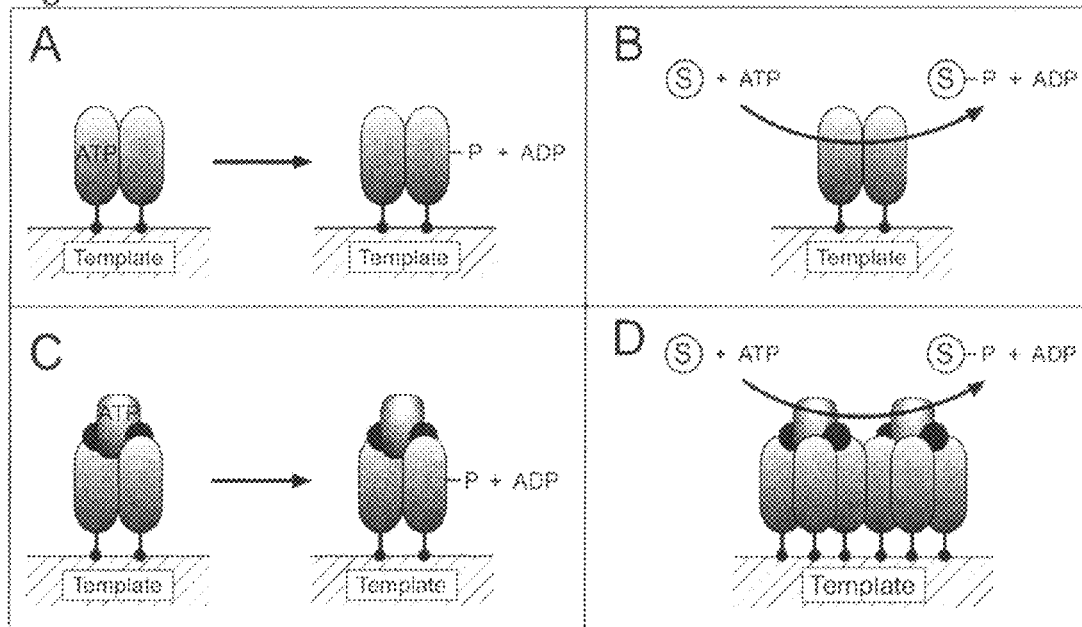
FIG. 2. Representative Embodiments
A: This figure represents an embodiment of the application applied to receptor tyrosine kinases (RTKs) and serine-threonine kinases. This embodiment assembles a receptor signaling domain that has autocatalytic capability in which it binds co-substrate, for example adenosine tri-phosphate, ATP, and catalyzes its own chemical modification, for example in the transfer of a phosphate group from ATP to form phosphorylated protein and adenosine di-phosphate, ADP.
B: This figure illustrates another embodiment of the application involving template-assembled receptor signaling domains, including those derived from RTKs, to catalyze a chemical reaction between two substrates, for example ATP and a phosphate-accepting substrate (S), to generate products, for example phosphorylated substrate (S-P) and ADP.
C: An embodiment of the application involving a template-assembled protein team, the formation of which is illustrated by FIGS. 1C and D. A signaling enzyme is recruited to the signaling team through interactions with the template-associated entity and/or an adaptor protein. The signaling enzyme binds substrate, for example ATP, as shown here, and catalyzes the chemical modification of the template-associated entity, for example, as in a phosphorylation reaction.
D: Another embodiment of the application involving a template-assembled protein team, which illustrated in FIG. 1D. A signaling enzyme is recruited to the signaling team through interactions with the template-associated entity and/or an adaptor protein. The signaling enzyme binds two substrates to catalyze the chemical modification of one substrate, for example the transfer of a phosphate group from ATP to the substrate, S, to generate phosphorylated substrate S-P and ADP.

In one embodiment, the measurable change results from a chemical modification to the polypeptide resulting from intrinsic enzymatic activity of the polypeptide as it interacts with the template. For example, in one embodiment, the polypeptide has intrinsic enzymatic activity, which leads to its chemical modification upon being attached to the template under suitable conditions. An example of this type of modification is the autophosphorylation, or more precisely an autophosphorylation reaction that occurs in trans, of receptor tyrosine kinase (RTK) domains (RTKs), as depicted in FIG. 2A. In another embodiment, the measurable change results from a chemical modification of a soluble substrate reagent present in the fluid that is catalyzed by the polypeptide as it interacts with the template, as depicted in FIG. 2B. This embodiment is exemplified by template-assembled RTKs that, with ATP, phosphorylate an added substrate molecule (depicted by the letter 'S' in FIG. 2B), such as for example poly[(glu)$_4$tyr](poly[SEQ ID NO: 2]) or a short peptide such as 'Axltide' (KKSRGDYMTMQIG(SEQ ID NO: 1)), where these substrate molecules become phosphorylated on the tyrosine (Y) residues. In yet another embodiment, the measurable change results from a chemical modification of a soluble substrate reagent that is catalyzed by enzymatic activity of a signaling enzyme present in the fluid that is recruited to the complex, as depicted in FIG. 2C. In still another embodiment, the measurable change results from a chemical modification to the polypeptide in a process catalyzed by a signaling protein that is recruited to the complex, as depicted in FIG. 2D. In still yet another embodiment, the measurable change results from a chemical modification of a soluble substrate reagent present in the fluid that results from a reaction cascade initiated by the polypeptide as it interacts with the template or a signaling enzyme that is recruited to the complex. A wide variety of membrane-associated protein systems are known that function in these exemplary ways and in a variety of other ways, and are contemplated by the present application. The application is not limited to a specific mechanism of protein action, but rather encompasses a wide variety of mechanisms that are achievable upon attachment of the polypeptide to a template that mimics the properties of the membrane environment.

As stated above, for the use of a complex to provide practical and useful information, the changes in the composition of the aqueous fluid in which the complex is contained that result from the activity of the assembled polypeptides, and other reagents when present, must be measurable. Examples of the types of changes that are readily measurable to provide useful information regarding the functionality and/or activity of the complex can include protein modifications, such as, for example, phosphorylation, acetylation, methylation, acylation, glycosylation, glycosylphosphatidylinositol (GPI) anchoring, sulfation, disulfide bond formation, deamidation, ubiquitination, sumoylation, and nitration of tyrosine. Alternatively, the complexed polypeptide or signaling cascade can produce other types of measurable changes in the test composition, such as, for example, activation of a fluorescent signal, changes in pH, measurable release of a reaction product or measurable utilization of a reagent initially present in the aqueous fluid. Of course, there are numerous other modifications that can be measured in various alternative embodiments of the application, depending upon the identity and functionality of the polypeptide and/or signaling cascade being tested.

A wide variety of measuring techniques can also be used, depending upon the type of modification being measured. For example, for measuring certain protein modifications, two-dimensional gel electrophoresis can be used to separate protein populations on the basis of charge and molecular weight. As one example of the use of electrophoresis, phosphorylation changes the protein charge and is often indicated by a horizontal trail of protein spots on a two-dimensional gel. In an analogous manner, changes in the separation properties of peptides that occur upon phosphorylation can be assessed by thin layer chromatography or high performance liquid chromatography, and thus be used to follow the progress of the modification. To study the modifications of a single protein, chromatographic purifications, antibody precipitations, or both, can be used to isolate sufficient amounts for testing. Once a protein has been isolated, a variety of techniques can be used to determine the modified amino acids. For example, in some cases, the precise molecular weight of the intact protein can be established by mass spectrometry ("MS"), which measures mass-to-charge ratio (m/z), yielding the molecular weight and the fragmentation pattern of peptides derived from proteins. MS represents a general method for all modifications that change the molecular weight. MS is especially useful if the protein isolated is not too heterogeneous, its mass is less than about 100 kDa, and it is in a buffer that is compatible with MS. As another example of modification measurement, amino-terminal protein sequencing by the classical technique of Edman degradation is useful for determining proteolytic processing. A wide variety of measurement techniques known in the art can be employed in connection with the application, the above examples representing just a few. By extension, any new measurement process that may be introduced to determine the progress of a reaction, a reaction that was measured formerly by methods established in prior art, can reasonably expected to be used in combination with the present application.

The measurement of choice for a given complex, such as, for example, spectrophotometric measurement of ATPase activity, or the incorporation of phosphate groups into test compounds, can be feasibly adapted for use in industry-standard automated plate readers, which can perform absorbance, fluorescence or luminescence readings on a large number of samples in parallel (such as, for example, from about 96 to about 1500 or more samples). It is apparent to those skilled in the art of high-throughput screening methods that template-assembled signaling complexes can be generated by semi-automatically and/or robotically dispensing the reagents, that include the templates, signaling components, and detection reagents, in a sequential fashion. Such an approach will also permit a synchronized initiation of the activity assay, and thus facilitate high-throughput analyses of the conditions that activate and regulate the signaling pathway in the template-assembled signaling system, including, but not limited to, screens for the effects of potential therapeutic agents, and in the manufacture of specialty reagents that are generated through the use of methods and materials described herein.

The template can take a variety of different forms, limited only by the need to provide a suitable platform to which polypeptides can be attached for appropriate interaction in accordance with the application. In one embodiment, the template is a free-standing template. As used herein, the term "free-standing" is used to mean that the template is not supported by an underlying supported material that is different in kind from the material that constitutes the template. In one embodiment, the free-standing template is a suspendable template. The term "suspendable" is intended to refer a template that can be dispersed homogeneously in an aqueous fluid for a period of time sufficient to use the template for its intended purpose as described herein.

One example of a free-standing template contemplated by the application comprises a lipid "vesicle" or "liposome." The terms "vesicle" and "liposome" are used interchangeably herein to refer to an assembly of lipids, which are a class of molecules either isolated from natural sources or are synthesized, that have the property of organizing into bilayer structures. For purposes of illustration, lipids can be formed into either 'small' unilamellar vesicles (SUVs) prepared by sonication, or 'large' unilamellar vesicles (LUVs) prepared by extrusion through the restrictions of filter pores. A vesicle can be formed of a single type of lipid, or can include a mixture of two or more different types of lipid molecules that are mixed together before vesicle formation. In one embodiment, a lipid vesicle is used that includes at least two different types of lipids, at least one of which is a nickel-chelating lipid. A vesicle that includes a nickel-chelating lipid is useful as a template in an assembly of histidine-tagged polypeptides onto the outer leaflet of the SUV or LUV membrane bilayer. Assembly of polypeptides onto such a lipid vesicle is also referred to herein as "vesicle binding." The organization of polypeptides produced by vesicle binding has been found to resemble the environment of the cell membrane inner leaflet sufficiently well to promote the assembly of active signaling complexes and to restore or significantly improve functionality of polypeptides in comparison to that of free polypeptides in a solution or suspension without such a template.

Other examples of suitable free-standing, suspendable substrates include, but are not limited to, other types of lipid assemblies, such as large multilamellar vesicles, self-assembled lipid nanotoubes, supported membranes, and also polymeric materials. Generally, such vesicles or other template architectures can comprise any compound or composition providing amphiphilic properties, capable of bilayer membrane formation, modified as described herein or as would otherwise be known in the art for specific binding affinity with a suitably-modified receptor component.

Another example of a free-standing template contemplated by the application is a polymer vesicle. The term "polymer vesicle" as used herein refers to a vesicle that has the same topological organization as one formed with lipids, but the membrane layer between the interior and exterior is composed of a synthetic polymer. Examples of polymers, which can be used to form vesicles include, but are not limited to polyethylene oxide-polyethylene diblock copolymers, polyethylene oxide-polybutadiene diblock copolymers, and polyethylene oxide-polypropylene oxide-polyethylene oxide triblock copolymers.

Yet another example of a free-standing template contemplated by the application is a polymer micelle. The term "polymer micelle" as used herein refers to a supramolecular noncovalent assembly that has the recognized organization of a micelle, as for example in a detergent micelle, with a hydrophobic interior and a hydrophilic exterior, and is instead composed of polymer molecules. Examples of polymers, which can be used to form micelles include, but are not limited to polyethylene oxide-polyethylene diblock copolymers and polyethylene oxide-polybutadiene diblock copolymers.

Still another example of a free-standing template contemplated by the application is a polymer molecule. The term "polymer molecule" as used herein refers to a molecule including repeating units joined together by covalent bonds. The polymer molecules that can provide the function of a template have in addition specific sites of attachment for proteins or polypeptides. Such polymers can be synthesized by a variety of methods, such as for example ring-opening metathesis polymerization, or can result from the derivitization of common, available polymers like dextran, branched polyethylene glycol and poly-l-lysine.

Still yet another example of a free-standing template contemplated by the application is a polymer bead. The term "polymer bead" as used herein refers to bead materials that are formed from chemically cross-linked polymers or otherwise self-associated polymers including, but not limited to, polystyrene, polyacrylamide, dextran and agarose.

Alternatively, a template can be formed on a solid substrate, or support (a heterogeneous format). Solid supports include, but are not limited to, supported lipid monolayer and bilayer membranes, self-assembled monolayers (SAMs) and the like. Such supported lipid membranes can be prepared by known methods, including, for example, deposition of monolayer and bilayer membranes on prepared substrates by Langmuir-Blodgett techniques, or through the fusion of vesicles to hydrophobic surfaces in the wells of immunoassay plates. In one example of a template supported on a solid substrate, the substrate is a glass slide. In another example of a template supported on a solid substrate, the substrate is a glass bead. Glass slides and glass beads suitable for use as described herein are readily available commercially. The glass used to form the glass slide or glass bead is preferably borosilicate glass. In another example of a template supported on a solid substrate, the substrate is a silicon wafer. The term "silicon wafer" as used herein refers to disc of silicon that is used in the electronics industry as the substrate for the manufacture of computer chips. In another example of a template supported on a solid substrate, the substrate is a silicon chip. The term "silicon chip" as used herein refers to a portion of a silicon wafer.

In another example of a template supported on a solid substrate, the substrate is a planar noble metal. In another example of a template supported on a solid substrate, the substrate is a colloidal noble metal. Planar noble metal substrates and colloidal noble metal substrates are also available commercially. In another example of a template supported on a solid substrate, the substrate is an oxide layer. The term "oxide layer" as used herein refers to for example the native oxide layer that grows on a surface of a silicon wafers ($SiO_2$), or various other metal oxides that can be fashioned as layers on surfaces, such as Indium Tin Oxide, or in the form of particles, such as Titanium oxide or Iron oxide. In another example of a template supported on a solid substrate, the substrate is a nanoparticle. The term "nanoparticle" as used herein refers to a colloidal particle that has dimensions no greater than 1000 nm across the largest dimension and more typically no larger than 100 nm across its largest dimension. In another example of a template supported on a solid substrate, the substrate is a polymer slab. In another example of a template supported on a solid substrate, the substrate is a polymer bead. Polymer films and polymer beads suitable for use as described herein are readily available commercially. The polymer used to form the polymer film or polymer bead is preferably polyacrylamide or polyethylene glycol or branched polyethylene glycol.

The polypeptide selected for use is one that corresponds to a membrane-associated protein of interest. The polypeptide can be an entire protein or a fragment of a protein. For example when the membrane-associated protein of interest is a trans-membrane protein, the polypeptide selected for attachment to a template is preferably a fragment composed of residues that do not span the cell membrane, i.e. a cytoplasmic (i.e., intracellular) fragment (CF), an extracellular fragment (EF), or more generally an extramembranous fragment. In the case of systems directed to cell trans-membrane receptor proteins, for example, the cytoplasmic fragment will often be the functional unit of the protein that is of interest. Furthermore, the polypeptide can be one that provides enzyme (catalytic) activity, that functions as a substrate, or that has recognition motifs for recruitment of other proteins or reagents, such as, for example, signaling and/or adaptor proteins.

With regard to receptor proteins, receptors are instrumental in recruiting cytoplasmic signaling elements, adaptor proteins, enzymes and membrane-associated proteins, into arrangements that modulate pathway activity. Accordingly, the template-assembly methods described herein are applicable to the study of these and other such signaling pathways. For example, Type I receptor proteins are organized with one or more structural domains, which are found on the both sides of the membrane and are joined by a transmembrane segment. An intracellular domain may often have enzymatic activity including tyrosine kinase activity, serine/threonine kinase activity, phosphotyrosine phosphatase, or phosphoserine/threonine phosphatase activity. The tyrosine kinase catalyzes the transfer of the y-phosphate group of adenosine triphosphate (ATP) to tyrosine moieties found within the receptor and to tyrosine containing substrates that dock onto the receptor. Various receptor systems have one or more of the properties of (i) recruitment, (ii) catalytic activity, and (iii) activity as a substrate. Generally speaking the receptors can have all the combinations of properties (i), (ii) and (iii).

Various classes of receptors that are subject to studies described herein include, without limitation, the following: Cytokine Type 1 receptors, Cytokine Type 2 receptors, GPI-anchored, Guanylyl Cyclase receptors, Interleukin-17 receptors, Integrins, Low-density lipoprotein (LDL) receptor and LDL receptor-related proteins, LINGO coreceptors for Nogo/p75, LRR-Ig Receptors, Netrin receptors, Neurexins, Notch, Patched, Plexins, Roundabout, Receptor-like protein tyrosine phosphatases (RPTPs), Receptor Tyrosine Kinases (RTK), Seven transmembrane (7TM) receptors, TGF-beta serine/threonine kinase receptors, Tetraspanins, TNF/NGF, and Toll.

In one aspect of the application, the membrane-associated protein under review is a multi-pass transmembrane protein. For example, with reference to the above list of receptors, receptor families 7TM and Patched include multi-pass transmembrane proteins. As used herein, the term "multi-pass" refers to a protein having more than one transmembrane domain, and thus includes one or more loops in the interior side or exterior side of the membrane. For example, 7TM receptors have seven discreet and highly predictable transmembrane domains. In one aspect of the application, the activity of a multi-pass transmembrane protein is analyzed by forming a complex in which the polypeptide corresponds to a loop of the protein, and is attached to the template at one or both ends. In another embodiment, multiple loops and/or fragments of a multi-pass protein are attached to the same template to allow for the loops and/or fragments to complex with one another, or to otherwise function together, to provide a desired activity for analysis.

Another class of receptors to which the present application is well suited is the class of proteins identified as Receptor Tyrosine Kinases (RTK). This large and diverse family of receptors exemplifies several general principles of receptor-ligand and receptor-receptor interactions. All members of the large receptor tyrosine kinase (RTK) family have a similar cytoplasmic catalytic domain that is activated by conformational changes upon ligand engagement whereas members within each subfamily have homologous extracellular domains. No RTKs are found in yeasts or plants. In mammals, multicellular organization is highly dependent on the proper functioning of RTKs as many RTKs have been reported to become oncogenic when their activity is altered. A tyrosine kinase is an enzyme that can transfer a phosphate group from ATP to a tyrosine residue in a protein. These enzymes are a subgroup of the larger class of protein kinases. Phosphorylation is an important function in signal transduction to regulate enzyme activity. The hormones that act on tyrosine kinase receptors are generally growth hormones and factors that promote cell division (i.e., insulin, insulin-like growth factor 1, epidermal-derived growth factor). These enzymes are involved in cellular signaling pathways and regulate key cell functions such as proliferation, differentiation, anti-apoptotic signaling and neurite outgrowth. Unregulated activation of these enzymes, through mechanisms such as point mutations or over-expression, can lead to various forms of cancer as well as benign proliferative conditions. The importance of RTKs in health and disease is further underscored by the existence of aberrations in PTK signaling occurring in inflammatory diseases and diabetes.

RTKs possess an extracellular ligand binding domain, a transmembrane domain and an intracellular catalytic domain. The transmembrane domain anchors the receptor in the plasma membrane, while the extracellular domains bind growth factors. Characteristically, the extracellular domains are comprised of one or more identifiable structural motifs, including cysteine-rich regions, fibronectin III-like domains, immunoglobulin-like domains, EGF-like domains, cadherin-like domains, kringle-like domains, Factor VIII-like domains, glycine-rich regions, leucine-rich regions, acidic regions and discoidin-like domains. The intracellular kinase domains of RTKs can be divided into two classes: those containing a stretch of amino acids separating the kinase domain and those in which the kinase domain is continuous. Activation of the kinase is achieved by ligand binding to the extracellular domain, which induces dimerization of the receptors. Receptors thus activated are able to autophosphorylate tyrosine residues outside the catalytic domain via cross-phosphorylation. The results of this auto-phosphorylation are stabilization of the active receptor conformation and the creation of phosphotyrosine docking sites for proteins which transduce signals within the cell. Signaling proteins which bind to the intracellular domain of receptor tyrosine kinases in a phosphotyrosine-dependent manner include RasGAP, P13-kinase, phospholipase C, phosphotyrosine phosphatase SHP and adaptor proteins such as Shc, Grb2 and Crk.

One type of RTK to which the present application has been advantageously applied is an Ephrin type-B receptor 2 precursor. Ephrin receptors and their ligands, the ephrins, mediate numerous developmental processes, particularly in the nervous system. Based on their structures and sequence relationships, ephrins are divided into the ephrin-A (EFNA) class, which are anchored to the membrane by a glycosylphosphatidylinositol linkage, and the ephrin-B (EFNB) class, which are transmembrane proteins. The Eph family of receptors are divided into 2 groups based on the similarity of their extracellular domain sequences and their affinities for binding ephrin-A and ephrin-B ligands. Ephrin receptors make up the largest subgroup of the receptor tyrosine kinase (RTK) family. The protein encoded by this gene is a receptor for ephrin-B family members.

Another type of RTK to which the present application has been advantageously applied is an Insulin receptor precursor. After removal of the precursor signal peptide, the insulin receptor precursor is post-translationally cleaved into two chains (alpha and beta) that are covalently linked. Binding of insulin to the insulin receptor (INSR) stimulates glucose uptake.

In the table below, receptors are classified according to taxonom, function and family. The list is not exhaustive, yet it serves to indicate the many examples of biological signal transduction that are conveyed through membrane-associated assemblies. The unifying principles of membrane protein organization and function, generates a reasonable expectation that the present application can be applied to these systems.

| Taxonom | Function | Family | Representative Ligands | Features |
|---|---|---|---|---|
| Prokaryotic | | | | |
| | Recruiters | Methyl-accepting Chemotaxis proteins | Aspartic acid, Ni, Co, serine, ribose, galactose, arginine, periplasmic binding proteins | Ligands include, light, various small molecules, pH, internally sensed redox potential. MCP-based systems mediate chemotaxis, social behavior, gene regulation |
| | Enzymes | Two-component sensor proteins | Osmolarity, nitrite, nitrate, phosphate | Primarily control transcription |
| Eukaryotic | | | | |
| | Recruiter with $2^{nd}$ messengers | 7TM | Gonadotropin, gonadotropin-releasing hormone, bradykinin, chemokines, dopamine, adrenergic reagents, light | Ligands from light to large proteins |
| Metazoan Specific | | | | |
| | Enzymes | Receptor Tyrosine Kinase | EGF, ephrins, FGF, PDGF, VEGF, neuregulins, insulin, IGF-1 | From close cell-cell interactions to endocrine signaling |
| | Enzymes | Ser-Thr kinase | TGF-b, BMPs, GDFs | Two to three co-receptors |
| | Enzymes | Guanyl cyclase | Natriuretic peptides | cGMP as $2^{nd}$ messenger |
| | Enzymes | RPTP | Midkine, pleiotrophin | Most receptors are orphans |
| | Recruiters | Toll | Bacterial lipopolysacharide | Innate immune recognition with NFκB activation |
| | Recruiters | LDL/LRP | LDL | Multiligand receptors that can serve as nutrient or signaling co-receptors |
| | Recruiters | Integrins | Extracellular matrix | Clustering upon ligand activation |
| | Recruiters | Roundabout | Slit | Repellant Interaction |
| | Recruiters | Plexins | Semaphorins | Receptors and ligands with sequence similarity |
| | Nuclear translocation | Notch | Delta | "One-time" receptor |
| | Transporter-like | Patched | Hedgehof-cholesterol complex | 12TM protein with a 7TM protein smoothened as partner |
| Chordate specific | | | | |
| | Recruiters | Cytokine type I | CH, prolactin (PRL), granulocyte macrophage-colony stimulating factor (GM-CSF), IL-2 | Four sets of subunits; α, β, γ, gp130; varying combinations |
| | Recruiters | TNF | TNF | Contain death domain |
| Vertebrate specific | | | | |
| | Recruiters | T cell receptor | Foreign antigens | Cooperate with presenting cells, CD4-CD8 |
| | Recruiters | Cytokine type 2 | IFNs, IL-10, IL-22 | Receptor heterodimers bind homodimeric ligands |

As stated above, a complex is provided by attaching one or more polypeptides to a template. In order to do so, it is typically necessary to first modify the polypeptide to include a linker moiety. As used herein, the term "linker moiety" is used to refer to a component effective to interact with the template to attach the polypeptide thereto. A wide variety of linker components are contemplated and a few examples thereof are described below, but these examples are in no way meant to limit the scope of the concept by which proteins and templates can be brought together as described herein.

Examples of ways the polypeptide can be modified to generate interaction between the polypeptide and the template, thereby engendering template-directed assembly, include the following, without limitation: the polypeptide can be designed to accept naturally occurring anchoring modifications; the polypeptide can be designed to engage in metal chelation, for example, by genetic engineering (histidine tag) or through the introduction of a synthetic chemical moiety that engages in chelation; the polypeptide can be engineered for specific covalent attachment to the template; the polypeptide can be engineered to attach a moiety that then engages in a specific covalent to the template; or the polypeptide can be engineered to include or be linked to an insertion domain.

Figure 3:
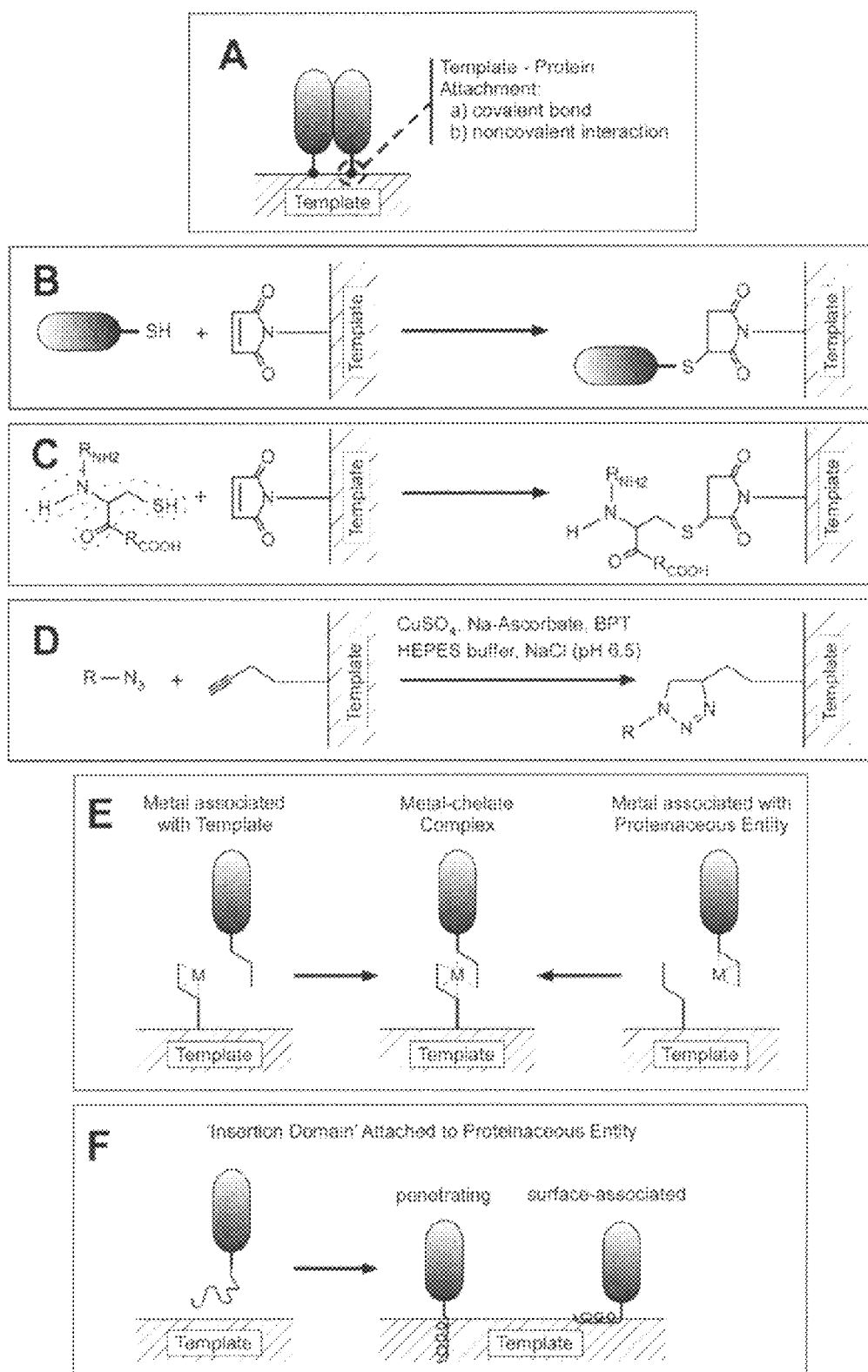
FIG. 3. Modes of Interaction with the Template
A: The proteinaceous entity has a point of attachment to the template, which can be generated either through the formation of a covalent bond between the proteinaceous entity and the template, or through a noncovalent interaction between the proteinaceous entity and the template.
B: A specific example of covalent attachment to the template in which a sulfhydryl group on the protein reacts with a maleimide moiety on the template.
C: A cysteinyl residue (encircled) within the polypeptide chain of a protein, a protein domain, a protein fragment or a peptide reacts with maleimide moiety to generate a covalent thioether linkage. $R_{NH2}$ and $R_{COOH}$ represent portions of the protein, protein domain, protein fragment or peptide that are N-terminal and C-terminal, respectively, to the cysteinyl residue.
D: Covalent attachment using the copper-catalyzed coupling of alkyne and azide groups. Prior to coupling, the azide moiety resides within the proteinaceous entity and the alkyne part of the template. In another embodiment (not shown), the alkyne moiety may reside within the proteinaceous entity and the azide moiety is attached to the template. BPT: bathophenanothroline disulfonate.
E: An illustration of a noncovalent metal-chelate-assisted interaction between the proteinaceous entity and the template. A metal or metal cation (M) is associated either with a moiety attached to the template (left) or a moiety attached to the proteinaceous entity (right). In both embodiments, M provides for a bridging interaction between the associated entity and the template (middle).

In one embodiment of the application, the linker component is effective to covalently bond to the template, as depicted schematically in FIGS. 3B, C & D. The linker component can be, for example, a genetically engineered segment including at least one amino acid that either permits the covalent attachment of the receptor fragment to the template, or the covalent attachment of a moiety that engenders specific attachment to the template. An example of the former includes the introduction of a cysteine (Cys) residue, which is known to exhibit specific reactivity toward maleimide, and reacts to form a covalent adduct. The maleimide moiety can be made available as the head group in a synthetic lipid molecule, and thereby facilitate direct covalent attachment of the receptor (via cysteine) to the template. An example of a second mode of attachment is illustrated by the introduction of a known biotinylation recognition sequence (e.g., MSGLNDIFEAQKIEWHE (SEQ ID NO: 3)) into a fusion protein, which is subsequently acted upon by E. coli biotin ligase (BirA) in the presence of biotin and ATP to covalently attach biotin into such a genetically-engineered receptor fragment. A biotin-modified receptor fragment may then be attached to the template via streptavidin, which binds with high affinity to both biotin groups in the template and to the biotin group receptor fragment.

In another embodiment, the linker component is effective to interact with the template noncovalently by metal chelation, as depicted schematically in FIG. 3E. In one embodiment, the metal or metal ion is associated with the template. The metal or metal ion can alternatively be associated with the linker component. In one preferred embodiment, the linker component comprises a genetically engineered histidine tag fused to the polypeptide. Templating is promoted through a specific noncovalent interaction with the modified phospholipid DOGS-NTA-Ni$^{2+}$. A histidine-tagged polypeptide randomly distributed in solution will orient on binding to a vesicle outer surface via the Ni-NTA-histidine interaction. Alternatively, fusion proteins may involve naturally-occurring binding domains that are effective to bind to certain lipid molecules, which by analogy to DOGS-NTA-Ni$^{2+}$, can be incorporated into the template. As another alternative, short peptides of known sequence can be incorporated into the template in a similar manner.

Complexes of this application can, in certain embodiments, comprise a membrane including a phospholipid component comprising a metal moiety selective for an amino acid residue of the fragment component. In certain embodiments, and as used to illustrate the broader aspects of this application, a nickel nitrilotriacetic acid moiety can be used to modify a phospholipid such as but not limited to 1,2-dioleoyl-sn-glycero-3-phosphocholine.

In another embodiment, the linker component is effective to interact with the template noncovalently by other complementary interactions. In another embodiment, the linker component is an insertion domain effective to interact with the template noncovalently by insertion of at least a portion of the domain into the template, as depicted schematically in FIG. 3F. The insertion domain can be of a type, for example, wherein at least a portion of the insertion domain interacts with the template by hydrophobic interactions. The insertion domain can be, for example, a genetically engineered peptidyl insertion domain. In another embodiment, the insertion domain comprises an anchoring moiety formed by the adaptation of a naturally occurring mechanism such as, for example, palmitoylation, myristoylation, prenylation, geranylation and GPI linkage.

Palmitoylation is the covalent attachment of fatty acids to cysteine residues of membrane proteins. Palmitoylation increases the hydrophobicity of proteins and contributes to their membrane association. It is a protein modification that is believed to be involved in the control of protein trafficking, localization, partitioning into domains, protein-protein interactions and functions. Palmitoylation of transmembrane proteins typically occurs on cysteine residues located in the border region between the transmembrane region (TMR) and the cytoplasmic domain. Palmitoylation of some proteins is reversible with cycles of acylation and deacylation. Some proteins are palmitoylated in vitro with Pal-CoA in the absence of any enzyme source (Dietrich and Ungermann, 2004). For example, a 100-fold enriched enzyme preparation (PAT) and the photoreceptor rhodopsin can reportedly be used as substrate to compare enzymatic and autocatalytic palmitoylation in vitro. Rhodopsin is palmitoylated with Pal-CoA alone, but addition of the enzyme preparation has been reported to increase the efficiency of acylation approximately 10-fold.

Myristoylation is an irreversible, post-translational protein modification found in animals, plants, fungi and viruses. In this protein modification, a myristoyl group (derived from myristic acid) is covalently attached via an amide bond to the alpha-amino group of an N-terminal glycine residue of a nascent polypeptide. The modification is catalyzed by the enzyme N-myristoyltransferase, and occurs most commonly on glycine residues exposed during co-translational N-terminal methionine removal. Myristoylation also occurs post-translationally, for example when previously internal glycine residues become exposed by caspase cleavage during apoptosis. Myristoylation plays a vital role in membrane targeting and signal transduction in plant responses to environmental stress.

Myristoylation is a very important lipid modification at the N-terminus of eukaryotic and viral proteins. It is involved in directing and anchoring proteins to membranes and, as a consequence, cellular regulation, signal transduction, translocation, several viral induced pathological processes and even apoptosis. The enzyme myristoylCoA:protein N-myristoyltransferase (NMT) recognizes certain characteristics within the N-termini of substrate proteins and finally attaches the lipid moiety to a required N-terminal glycine.

Prenylation or isoprenylation is the addition of hydrophobic molecules to a protein to facilitate its attachment to the cell membrane. The result is similar to that of all lipid anchored proteins (e.g. the GPI anchor). All isoprenylation chains are products of the HMG-CoA reductase pathway: geranylgeraniol (GG), farnesol and dolichol.

A GPI anchor or glycosylphosphatidylinositol is a common posttranslational modification of the C-terminus of membrane-attached proteins. It is composed of a hydrophobic phosphatidyl inositol group linked through a carbohydrate containing linker (glucosamine and mannose linked to phosphoryl ethanolamine residue) to the C-terminal amino acid of a mature protein. The two fatty acids within the hydrophobic phosphatidyl-inositol group anchor the protein to the membrane.

During natural processing, glypiated proteins contain a signal peptide, thus directing them into the endoplasmic reticulum (ER). The C-terminus is composed of hydrophobic amino acids which stay inserted in the ER membrane. The hydrophobic end is then cleaved off and replaced by the GPI-anchor. As the protein processes through the secretory route, it is transferred via vesicles to the Golgi and finally to the extracellular space where it remains attached to the exterior leaflet of the cell membrane. Since the glypiation is the sole means of attachment of such proteins to the membrane, cleavage of the group by phospholipases will result in controlled release of the protein from the membrane. The latter mechanism is used in vitro, i.e. the membrane proteins released from the membranes in the enzymatic assay are glypiated protein.

Phospholipase C is an enzyme that is known to cleave the phospho-glycerol bond found in GPI-anchored proteins. Treatment with PLC will cause release of GPI-linked proteins from the outer cell membrane. The T-cell marker Thy-1, acetylcholinesterase, as well as both intestinal and placental alkaline phosphatase are known to be GPI-linked and are released by treatment with PLC. GPI-linked proteins are thought to be preferentially located in lipid rafts, suggesting a high level of organization within microdomains plasma membrane.

As described above, the present application involves the use of a homo- or heterogeneous template to assemble polypeptides, such as, for example, polypeptides derived from membrane-associated proteins, and optionally additional reagents, to provide a functional complex exhibiting the biochemical activity of a membrane-associated protein or protein system, such as, for example, a signaling pathway. The complex can be used to analyze the effect of an active agent on the functionality of the protein or protein system, to analyze the effect of a mutation on the protein or protein system, or to produce reaction products of value in a novel manufacturing process. One embodiment of such a method comprises (1) providing a template configured for attachment of a polypeptide in an aqueous medium; (2) introducing a polypeptide to the medium, the polypeptide having a linker component attached thereto; (3) complexing the polypeptide with the template, and optionally one or more additional components, such as, for example a signaling protein, an adaptor protein or a receptor domain with enzymatic activity; and (4) introducing a test compound into the fluid. In one embodiment, the template is provided by providing a phospholipid component in a medium suitable for vesicle formation, such a component comprising a cationic metal moiety selective for chelation of an amino acid residue, and the polypeptide includes at least one amino acid with affinity for selective coupling bonding or chelating interaction with the phospholipid component. In another embodiment, the polypeptide is covalently bound to the template. In yet another embodiment, the linker component is an insertion domain that interacts with the template to attach the polypeptide to the template.

As stated above, the complex can optionally include additional reagents such as, for example, one or more of a signaling protein, an adapter protein, and/or other membrane-associated components, including other naturally-occurring or synthetic lipids. As used herein, the term "signaling protein" refers to a protein that is part of a cellular signal transduction pathway. In certain embodiments, the signaling protein can be a kinase of the growth factor, or cytokine signaling pathway. The term "adaptor protein" is used to refer to a protein, which is part of a signal transduction pathway, which helps to recruit other proteins in the pathway to the membrane. The signaling protein is typically an enzyme active in or having a role in a particular cellular signal transduction pathway. Where conducive to biochemical activity, such a complex can comprise a mixture of receptor fragments and/or other membrane-associated components, including other naturally occurring lipids and adaptor proteins.

Templates are expected, and shown in the Examples described below, to be compatible with reagents currently used in the assay of enzyme activity. By reference to the Table below, the templates were combined with these other reagents in a solution, and under such conditions generated significant improvements in biochemical functionality. More generally, liposomes, polymerosomes and other templates are expected to be robust and perform in the aqueous solutions in which the biochemical test reagents and proteins are dissolved and assayed (Discher and Eisenberg, 2002; Duzgunes, 2003, 2004).

Table of Conditions used to Assay Receptor Tyrosine Kinases

| Insulin Receptor | EphB2 | Tie2 |
| --- | --- | --- |
| 55 mM Tris-HCl | 2 mM Tris-HCl | 4 mM Tris-HCl |
| 15 mM NaCl | 6 mM NaCl | 12 mM NaCl |
| 10 µM EGTA | 4 µM EGTA | 8 µM EGTA |
| 0.003% Brij-35 | 0.0018% Brij-35 | 0.003% Brij-35 |
| 27 mM Sucrose | 10.8 mM Sucrose | 21.6 mM Sucrose |
| 20 µM PMSF | 8 µM PMSF | 16 µM PMSF |
| 100 µM Benzamidine | 40 µM Benzamidine | 80 µM Benzamidine |
| 0.01% BME | 0.004% BME | 0.008% BME |
| 100 mM Sodium Orthovanadate | 8.2 mM MOPS | 8.4 mM MOPS |
| 8.4 mM MOPS | 0.1 mg/mL polyGlu$_4$Tyr | 0.1 mg/mL polyGlu$_4$Tyr |
| 25 µM Axltide | 10 mM MnCl$_2$ | 0, 0.125, 0.25, or 0.5 mM MnCl$_2$ |
| 0.1% glycerol | 0.3% glycerol | 0.01% glycerol |
| 270 nM Insulin Receptor RTK | 77 nM EphB2 RTK domain | 136 nM Tie2 RTK domain |

-continued

Table of Conditions used to Assay Receptor Tyrosine Kinases

| | | |
|---|---|---|
| domain | 60 µg/mL BSA | 20 µg/mL BSA |
| 20 µg/mL BSA | 60 µM TCEP | 20 µM TCEP |
| 20 µM TCEP | 90 µM ATP | 90 µM ATP |
| 90 µM ATP | 13.5 mM $MgCl_2$ | 13.5 mM $MgCl_2$ |
| 13.5 mM $MgCl_2$ | | |
| TEMPLATES Vesicles: | TEMPLATES Vesicles: | TEMPLATES Vesicles: |
| 1.7 µM DOGS-NTA-$Ni^{2+}$ | 1.2 µM DOGS-NTA-$Ni^{2+}$ | 1.9 µM DOGS-NTA-$Ni^{2+}$ |
| 1.7 µM DOPC | 1.2 µM DOPC | 1.9 µM DOPC |

Assays using methods and materials as described herein are conducted in a manner similar to that which is known to those skilled in the art of biochemical signaling pathways, and typically follows standard practices, except for the introduction of template reagent in amounts appropriate for the assay.

Reference will now be made to the following Examples, which describe laboratory work that has been performed in support of this application. It is understood that no limitation to the scope of the application is intended thereby. The Examples are provided solely to promote a full understanding of the concepts embodied in the application.

EXAMPLES

In the illustrative examples described below, the concepts described herein are applied to five protein reagents, which comprised purified or partly purified recombinant proteins. Each comprised a different receptor tyrosine kinase (RTK) domain from the Insulin Receptor, the Axl Receptor, the EphB2 Receptor, the ErbB4 receptor, or the Tie2 receptor. All five RTK domains were purchased from Upstate Cell Signaling Solutions Inc. (www.upstate.com/; catalog #: Insulin Receptor, 14-466; Axl Receptor, 14-512; EphB2, 14-553; ErbB4, 14-569; Tie2, 14-540) and had been engineered, for the purpose to aid in purification a hexahistidine tag at the N-terminus of the RTK domain.

In the examples described herein, the hexahistidine tag was used to facilitate an interaction with a template. In the examples described here, templates were lipid vesicles prepared by the method of extrusion, and were comprised of a 1:1 molar ratio of DOPC and DOGS-NTA-$Ni^{2+}$. DOGS-NTA-$Ni^{2+}$ provided the specific affinity for the hexahistidine tag at the N-terminus of the RTK domain, and generated the novel templating interaction that resulted in the improved functionality afforded by the present application. Further background information relating to the experimental work described below is provided in U.S. Patent Application Publication No. 2005/0148038, which is hereby incorporated by reference herein in its entirety.

Receptor tyrosine kinase domains were tested for autophosphorylating and substrate phosphorylating activities in solution, and in the presence of vesicle templates, under the reaction conditions described in the table above. The procedures were patterned after those used for assaying the reagents in solution, with the exception of the addition of template. No additional incubation periods were required. In all situations the progress of the reaction was measured by phosphate group incorporation, which resulted from the transfer of $^{32}$P-labeled gamma phosphate groups from ATP to either tyrosine moieties within the RTK domain itself, or to tyrosine moieties of substrate reagents, which were, in these examples, either poly($[glu]_4tyr)_n$(poly(SEQ ID NO: $20_n$) or Axltide. The amount of $^{32}$P-phosphate incorporated in all these examples was measured by calibrated scintillation as acid-precipitatable phosphate trapped on disks of filter paper, according to standard procedures known to those skilled in the art.

Example 1

Insulin Receptor Autophosphorylation and the Preparation of Phosphorylated Insulin Receptor RTK Domain FIG. 5A shows the differences in the extent of phosphate group incorporation, after a ten minutes, for reactions conducted the absence of template (in solution) versus reactions conducted in the presence of template. In addition, the reactions were conducted in the presence of the substrate peptide, Axltide, (columns one and two in FIG. 5A), and also in the absence of the Axltide substrate (columns three and four in FIG. 5A). In the absence of the substrate peptide, the incorporation of phosphate is a result of RTK autophosphorylation, which refers to a reaction in which phosphate groups are transferred to certain tyrosine residues in the RTK domain. In this example, the RTK domain is particularly effective at autophosphorylation in the presence of template (last column) and particularly ineffective at autophosphorylation in the absence of template (third column). In a second instance of this reaction, which is provided in support of efficient Insulin Receptor RTK domain autophosphorylation, the data in FIG. 6 are provided. Here also, the autophosphorylation was ineffective in solution, and showed no incorporation over nonspecific background samples. Thus, the improvement factor for autophosphorylation shown in FIG. 6 (Insulin—AutoP, 18,000%) represents the increase over this background incorporation. The amount of phosphate group incorporation in the presence of template is evidence that the template provides for an efficient means to synthesize phosphorylated Insulin receptor RTK domain. The application thus provides a novel means to manufacture this reagent, which is not possible with current methods.

Example 2

Improved Regulation of Tie2 RTK Domain Activity, Engendered by Template

FIG. 5B and FIG. 5C depicts the influence of template on the tyrosine kinase activity of the Tie2 RTK domain. The tyrosine kinase activity of the Tie2 RTK domain was measured in the presence of a phosphate-accepting substrate, in this example poly($[glu]_4tyr)_n$(poly(SEQ ID NO: $2_n$) (FIG.

5B), and in its absence, which measured RTK domain autophosphorylation (FIG. 5C). FIGS. 5B and C represents the amount of acid precipitatable phosphate after a 10 minute reaction, as a function of various concentrations of the reagent $MnCl_2$. These results show that the effect of template can be influenced by the reaction conditions, and provide evidence that the performance of the system can be improved through systematic variations of these conditions, which are known to those skilled in the art.

In the presence of template, the autophosphorylation of the Tie2 RTK domain (FIG. 5C) increases 9-fold at the 0.5 mM Manganese Chloride concentration. As in Example 1, this example demonstrates that the use of the template provides for a new method to prepare phosphorylated protein reagent: phosphorylated Tie2 RTK domain.

This example also depicts improvements in the biochemical functionality of the Tie2 RTK domain, which is engendered by the introduction of template. FIG. 5B shows the total phosphate incorporation, which was regarded as the amount of acid-precipitatable phosphate in the presence of Tie2 RTK domain and the substrate poly([glu]$_4$tyr)$_n$(poly(SEQ ID NO: 2)$_n$). Template serves to lower total phosphate group incorporation compared to the situation in the absence of template (in solution) (FIG. 5B). A comparison of FIG. 5B to FIG. 5C provides evidence that phosphate group incorporation at 0.5 mM Manganese Chloride, in the presence of substrate and template (FIG. 5B right column of the pair), is equal to the phosphate group incorporation at 0.5 mM Manganese Chloride in the absence of substrate and in the presence of template (FIG. 5C right column of the pair). It can thus be deduced from these results that autophosphorylation is the principal reaction event in the presence of template, whether or not substrate is also present. Consequently, the efficient autophosphorylation of the Tie2 RTK domain (FIG. 5C right columns of each pair) leads to inhibition of RTK domain activity and substrate (Poly([glu]$_4$tyr)$_n$) phosphorylation. This observation is consistent with current thinking on the regulation of Tie2 RTK activity by autophosphorylation, which is that the autophosphorylation event results in auto-inhibition of kinase activity. We infer that the Tie2 RTK domain is not properly regulated in solution, but that via autophosphorylation, which promoted by the template, becomes properly regulated. The application thus provides a means for improving the biological functionality RTK domains. Receptor tyrosine kinase activity of an RTK domain can either be activated or inhibited by autophosphorylation. In the case of the Tie2 RTK domain, activity is inhibited by autophosphorylation. In the case of the Insulin receptor, activity is increased by autophosphorylation. The application provides a means to improve the biological functionality in both of these, as well as other situations.

Example 3

Generality of the Effect of Template on RTK Domain Activity

In this example (FIG. 6), the introduction of template is demonstrated to improve the activity of RTK domains from the EphB2 receptor (FIG. 6, top), the Axl receptor (FIG. 6, second from top), the ErbB4 receptor (FIG. 6, third from top) and the Insulin Receptor (FIG. 6, bottom). In each of these cases the introduction of templates improved the tyrosine kinase activities of the RTK domains in the absence of additional substrate (AutoP), that is to say in the autophosphorylation mode, and also in the presence of an added phosphate accepting substrate, either Axltide (with Axl and the Insulin receptor) or poly([glu]$_4$tyr)$_n$ (poly(SEQ ID NO: 2)$_n$) (EphB2 and Erb4). Improvements ranged between 20% and 700% in the presence of the substrate, and between 70% and 18,000% in the process of autophosphorylation.

The present application contemplates modifications as would occur to those skilled in the art without departing from the spirit of the present invention. In addition, the various procedures, techniques, and operations may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Any reference to a specific direction, for example, references to up, upper, down, lower, and the like, is to be understood for illustrative purposes only or to better identify or distinguish various components from one another. Unless specifically identified to the contrary, all terms used herein are used to include their normal and customary terminology. Further, while various embodiments having specific components and structures are described and illustrated herein, it is to be understood that any selected embodiment can include one or more of the specific components and/or structures described for another embodiment where possible.

While multiple embodiments have been described in detail in the foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present application and should not be construed to limit or restrict the scope of the claims set forth below. Further, any theory, mechanism of operation, proof, or finding stated herein is meant to further enhance understanding of the concepts described herein and is not intended to limit the present application in any way to such theory, mechanism of operation, proof, or finding. In reading the claims, words such as "a," "an," "at least one" and "at least a portion" are not intended to limit the claims to only one item unless specifically stated to the contrary. Further, when the language "at least a portion" and/or "a portion" is used, the claims may include a portion and/or the entire item unless specifically stated to the contrary.

REFERENCES

Alarcon, B., Gil, D., Delgado, P., and Schamel, W. W. (2003). Initiation of TCR signaling: regulation within CD3 dimers. Immunol Rev 191, 38-46.

Bazan-Socha, S, Bukiej, A, Marcinkiewicz, C, and Musial, J. (2005). Integrins in pulmonary inflammatory diseases. Curr Pharm Des 11, 893-901.

Ben-Shlomo, I., Yu Hsu, S., Rauch, R., Kowalski, H. W., and Hsueh, A. J. (2003). Signaling receptome: a genomic and evolutionary perspective of plasma membrane receptors involved in signal transduction. Sci STKE 2003, RE9.

Brandts, J. F., and Jacobson, B. S. (1983) A general mechanism for transmembrane mechanism for transmembrane signaling based on clustering of receptors. Syn. Surv. Path. Res. 2, 107-114.

Dietrich, L. E. P., and Ungerman, C. (2004) On the mechanism of protein palmitoylation. EMBO Reports 5,1053-1057.

Duzgunes, N. ed. (2003) Liposomes, Part A, Methods in Enzymology, Vol. 367 (Amsterdam: Elsevier/Academic Press).

Duzgunes, N. ed. (2004) Liposomes, Part D, Methods in Enzymology, Vol. 387 (Amsterdam: Elsevier/Academic Press).

Discher, D. E., and Eisenberg, A. (2002) Polymer Vesicles. Science 297, 967-973.

Garcia, K., ed. (2004). Cell Surface Receptors. Advances in Protein Chemistry, vo. 68, Richards, F. M., Eisenberg, D. S., and Kuriyan, J., Series Eds. (Amsterdam: Elsevier/Academic Press).

Heldin, C. H. (1995). Dimerization of cell surface receptors in signal transduction. Cell 80, 213-223.

Mann, M., and Jensen, O. N. (2003). Proteomic analysis of post-translational modifications. Nat Biotechnol 21, 255-261.

Martin, M. U., and Wesche, H. (2002). Summary and comparison of the signaling mechanisms of the Toll/interleukin-1 receptor family. Biochim Biophys Acta 1592, 265-280.

Mui, B., Chow, L., and Hope, M. J. (2003) Extrusion techniques to generate liposomes of defined size in Liposomes, Part A, Methods in Enzymology, Vol. 367, Duzgunes, N. ed. (Amsterdam: Elsevier/Academic Press).

Niu, X.-L., Peters, K. G., and Kontos, C. D. (2002) Deletion of the carboxyl terminus of Tie2 enhances kinase activity, signaling and function. J. Biol. Chem. 277, 31768-31773.

Pawson, T., and Nash, P. (2003). Assembly of cell regulatory systems through protein interaction domains. Science 300, 445-452.

Penuel, E., Schaefer, G., Akita, R. W., and Sliwkowski, M. X. (2001). Structural requirements for ErbB2 transactivation. Semin Oncol 28, 36-42.

Robertson, S. C., Tynan, J. A., and Donoghue, D. J. (2000). RTK mutations and human syndromes when good receptors turn bad. Trends Genet 16, 265-271.

Singer, S. J., and Nicolson, G. L. (1972). The fluid mosaic model of the structure of cell membranes. Science 175, 720-731.

Shrout, A. L., Montefusco, D. J., and Weis, R. M. (2003). Template-directed assembly of receptor signaling complexes. Biochemistry 42, 13379-13385.

Stroud, R. M., and Wells, J. A. (2004). Mechanistic diversity of cytokine receptor signaling across cell membranes. Sci STKE 2004, re7.

```
                        SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: SEQ ID NO: 1 is a commercially available
      substrate available from Upstate Cell Signaling Solutions, Inc. as
      product number 12-516

<400> SEQUENCE: 1

Lys Lys Ser Arg Gly Asp Tyr Met Thr Met Gln Ile Gly
1               5                   10

<210> SEQ ID NO 2
<211> LENGTH: 5
<212> TYPE: PRT
<213> ORGANISM: Artificial Sequence
<220> FEATURE:
<223> OTHER INFORMATION: SEQ ID NO: 2 is a repeating unit in
      poly([Glu]4Tyr), and includes 4 Glu residues and 1 Tyr residue in
      random order.  Thus, each of residues Xaa at positions 1-5 is Glu
      or Tyr, provided that only one is Tyr and the remaining four are
      Glu.
<220> FEATURE:
<221> NAME/KEY: UNSURE
<222> LOCATION: (1)..(5)
<223> OTHER INFORMATION: SEQ ID NO: 2 is a repeating unit in
      poly([Glu]4Tyr), which is commercially available from Sigma-
      Aldrich as product number P7244. The P7244 product is believed to
      include 9-35 repeated units of the polypeptide of SEQ ID NO: 2.

<400> SEQUENCE: 2

Xaa Xaa Xaa Xaa Xaa
1               5

<210> SEQ ID NO 3
<211> LENGTH: 17
<212> TYPE: PRT
<213> ORGANISM: Artificial Sequence
```

-continued

```
<220> FEATURE:
<223> OTHER INFORMATION: SEQ ID NO. 3 is operable as a biotinylation
      recognition sequence that operates in a fusion protein to
      covalently bind biotin. SEQ ED NO. 3 is a consensus sequence
      derived from proteins that are substrates for E. coli biotin
      ligase (BirA).

<400> SEQUENCE: 3

Met Ser Gly Leu Asn Asp Ile Phe Glu Ala Gln Lys Ile Glu Trp His
1               5                   10                  15

Glu
```

What is claimed is:

1. A method for analyzing in vitro the effect of a molecule upon a polypeptide-catalyzed reaction or cascade, comprising:
   providing an aqueous fluid including:
      one or more reagent; and
      a biologically active complex including a synthetic lipid membrane-like template and at least one membrane-associated polypeptide attached to the template, wherein the complex is functional under a given set of conditions to produce a measurable modification in the content of said one or more reagent or in said polypeptide;
   introducing a fluid a test molecule selected from the group consisting of a drug, a drug candidate, an agonist and an antagonist; and
   measuring the modification to determine the effect of the test molecule on the reaction or cascade.

2. The method in accordance with claim 1 wherein the test molecule is selected from the group consisting of a drug, a drug candidate.

3. The method in accordance with claim 1 wherein the measurable modification results from a process selected from the group consisting of (1) a chemical modification to the polypeptide resulting from intrinsic enzymatic activity of the polypeptide as it interacts with the template, (2) chemical modification of a soluble substrate reagent present in the fluid that is catalyzed by the polypeptide as it interacts with the template, (3) chemical modification of a soluble substrate reagent that is catalyzed by enzymatic activity of a signaling enzyme present in the fluid that is recruited to the complex, (4) chemical modification to the polypeptide in a process catalyzed by a signaling protein that is recruited to the complex, and (5) chemical modification of a soluble substrate reagent present in the fluid that results from a reaction cascade initiated by the polypeptide as it interacts with the template or a signaling enzyme that is recruited to the complex.

4. The method in accordance with claim 3 wherein the polypeptide comprises a receptor tyrosine kinase domain, and wherein the process comprises autophosphorylation of the receptor tyrosine kinase domain.

5. The method in accordance with claim 1 wherein the measurable modification is a modification selected from the group consisting of phosphorylation, dephosphorylation, acetylation, methylation, acylation, glycosylation, glycosylphosphatidylinositol (GPI) anchoring, sulfation, disulfide bond formation, deamidation, ubiquitination, sumoylation nitration of tyrosine, hydrolysis of ATP or GTP activation of a fluorescent signal, release of a reaction product and utilization of a reagent initially present in the fluid.

6. The method in accordance with claim 1 wherein the template is supported on a solid substrate material.

7. The method in accordance with claim 6 wherein the substrate is selected from the group consisting of a glass slide, a glass bead, a silicon wafer, a silicon chip, a planar noble metal, a colloidal noble metal, a metal oxide layer, a nanoparticulate material, a polymer slab, a polymer film and a polymer bead.

8. The method in accordance with claim 6 wherein the template is selected from the group consisting of a phospholipid bilayer, a phospholipid monolayer and a polymer film.

9. The method in accordance with claim 1 wherein the polypeptide has attached thereto a linker component effective to attach the polypeptide to the template.

10. The method in accordance with claim 9 wherein the linker component is selected from the group consisting of a component effective to covalently bond to the template, a component effective to interact with the template noncovalently by metal chelation, a component effective to interact with the template noncovalently by other complementary interactions, and an insertion domain effective to interact with the template noncovalently by insertion of at least a portion of the domain into the template.

11. The method in accordance with claim 9 wherein the linker component comprises a component effective to interact with the template noncovalently by metal chelation, and wherein the metal or metal ion is associated with the template.

12. The method in accordance with claim 9 wherein the linker component comprises a component effective to interact with the template noncovalently by metal chelation, and wherein the metal or metal ion is associated with the linker component.

13. The method in accordance with claim 9 wherein the linker component comprises a genetically engineered histidine tag.

14. The method in accordance with claim 9 wherein the linker component comprises an insertion domain.

15. The method in accordance with claim 14 wherein the insertion domain is effective to interact with the template noncovalently by insertion of at least a portion of the domain into the template, and wherein at least a portion of the insertion domain interacts with the template by hydrophobic interactions.

16. The method in accordance with claim 14 wherein the insertion domain comprises a genetically engineered peptidyl insertion domain.

17. The method in accordance with claim 14 wherein the insertion domain comprises an anchoring moiety formed by the adaptation of naturally occurring mechanisms.

18. The method in accordance with claim 17 wherein the naturally occurring mechanism is selected from the group consisting of palmitoylation, myristoylation, prenylation, geranylation, GPI linkage and a synthetic analog thereof.

19. A method for analyzing in vitro the effect of a molecule upon a polypeptide-catalyzed reaction or cascade, comprising:
   providing an aqueous fluid including:
      one or more reagent; and
      a biologically active complex including a synthetic lipid membrane-like template and at least one membrane-associated polypeptide attached to the template, wherein the complex is functional under a given set of conditions to produce a measureable modification in the content of said one or more reagent or in said polypeptide;
   introducing into the fluid a test molecule selected from the group consisting of a drug, a drug candidate, an agonist and an antagonist; and
   measuring the modification to determine the effect of the test molecule on the reaction or cascade;
   wherein the template is a free-standing template.

20. The method in accordance with claim 19 wherein the template is selected from the group consisting of a lipid vesicle, a polymer vesicle, a polymer micelle, a polymer molecule, and a polymer bead.

\* \* \* \* \*